United States Patent [19]

Soreq et al.

[11] Patent Number: 5,595,903
[45] Date of Patent: Jan. 21, 1997

[54] GENETICALLY ENGINEERED HUMAN ACETYLCHOLINESTERASE

[75] Inventors: Hermona Soreq, Rishon Le Zion; Zakut Haim, Savion, both of Israel

[73] Assignee: Yissum Research Development Co. of the Hebrew University of Jerusalem, Jerusalem, Israel

[21] Appl. No.: 111,314

[22] Filed: Aug. 2, 1993

Related U.S. Application Data

[63] Continuation of Ser. No. 496,554, Mar. 20, 1990, abandoned.

[30] Foreign Application Priority Data

Mar. 21, 1989 [IL] Israel ............................................ 89703

[51] Int. Cl.$^6$ ............................. C12N 5/00; C12N 15/00; C12N 9/18
[52] U.S. Cl. .................. 435/240.2; 435/197; 435/370.1; 435/252.3; 536/23.2; 536/23.5
[58] Field of Search .............................. 435/320.1, 252.3, 435/240.2; 536/23.2, 23.5

[56] References Cited

U.S. PATENT DOCUMENTS

5,248,604  9/1993  Fischer ................................. 435/197

FOREIGN PATENT DOCUMENTS

0206200  12/1986  European Pat. Off. ............... 435/197

OTHER PUBLICATIONS

Weitz et al., *Biochim et Biopys Acta*, 776:56–74, 1984.
Prody et al, *PNAS*, vol. 84 3555–3559, Jun. 1987.
Shumacher et al., *Nature*, vol. 319:405–409, Jan. 30, 1986.
Young et al, *PNAS*, vol. 80, Mar., 1983, pp. 1194–1198.

*Primary Examiner*—Robert A. Wax
*Assistant Examiner*—Keith D. Hendricks
*Attorney, Agent, or Firm*—Pennie & Edmonds

[57] ABSTRACT

Genetically engineered human acetylcholinesterase and antibodies that define the protein are described. These composition may be used in pharmaceutical preparations for treatment and prophylaxis of organo-phosphorous compound poisoning or post-operative apnea. Also described are human cholinesterase DNA probes which may be employed for diagnosing progressing ovarian carcinomas and hemocytopoietic disorders.

19 Claims, 32 Drawing Sheets

As: Active site
Ct: C'-terminus

```
           10         20         30         40         50         60
     ATGTGGAACC CCAACCGTGA GCTGAGCGAG GACTGCCTGT ACCTCAACGT GTGGACACCA 70         80         90        100        110        120
     TACCCCCGGC CTACATCCCC CACCCCTGTC CTCGTCTGGA TCTATGGGGG TGGCTTCTAC
                          ⊖

130        140        150        160        170        180
     AGTGGGGCCT CCTCCTTGGA CGTGTACGAT GGCCCCTTCT TGGTACAGGC CGAGACCACT
                       3' CTCCACATCCTACCGCC 5'

190        200        210        220        230        240
     GTGCTGGTGT CCATGAACTA CGGGGTGGGA GCCTTTGGCT TCCTGGCCCT GCCGGGGAGC 250        260        270        280        290        300
     CGAGAGGCCC CGGGCAATGT GGGTCTGGTG GATCAGAGGC TGGCCCTGCA GTGGGTGCAG

5'          ⊕ ← 3'
          310        320        330        340        350        360
     GAGAAACTGG CAGCCTTCGG GGGTGACCCG ACATCAGTGA CGGTCTTTGG GGAGAGCGCG 370        380        390        400        410        420
     GGAGCGGCCT CGGTGGGCAT GCACCTGCTG TCCCCGCCCA GCCGGGGCCT GTTCCACAGG 430        440        450        460        470        480
     GGCGTGCTGC AGAGCGGTGC CCCCAATGGA CCCTGGGCCA CGGTGGGCAT GGGAGAGGCC 490        500        510        520        530        540
     CGTCGCAGGG CCACGCAGCT GGCCCACCTT GTGGGCTGTC CTCCAGGCGG CACTGGTGGG
                                                                ⊕←
          550        560        570        580        590        600
     AATGACACAG AGCTGGTAGC CTGCCTTCGG ACACGACCAG CGCAGGTCCT GGTCGACCAC
                                                              3' TTGGTG
          610        620        630        640        650        660
     GAATGGCACG TGCTGCCTCA AGAAAGCGTC TTCCGGTTCT CCTCCGTGCC TGTGGTAGAT
     CTTACCGTGC A 5'

670 ←⊕      680        690        700        710        720
     GGAGACTTCC TCAGTGACAC CCCAGAGGCC CTCATCAACG CGGGAGACTT CCACGGCCTG 730        740        750        760        770        780
     CAGGTGCTGG TGGGTGTGGT GAAGGATGAG GGCTCGTATT TTCTGGTTTA CGGGGCCCCA 790        800        810        820        830        840
     GGCTTCAGCA AAGACAACGA GTCTCTCATC AGCCGGGCCG AGTTCCTGGC CGGGGTGCGG
```

FIG. 1c

```
       850        860        870 ⊕ ←   880        890        900
GTCGGGGTTC CCCAGGTAAG TGACCTGGCA GCCGAGCCTG TGGTCCTGCA TTACACAGAC 910        920        930        940        950        960
TGGCTGCATC CCGAGGACCC GGCACGCCTG AGGGAGGCCC TGAGCGATGT GGTGGGCGAC
           ← ⊖
       970        980        990       1000       1010       1020
CAC AATGTCG TGTGCCCCGT GGCCCAGCTG GCTGGGCAGA CTGGCTGCCC AGGGTGCCCG
 3' TACAGC  ACACGGGGCA 5'

1030       1040       1050       1060       1070       1080
GGTACTACGC CTAACGTCTT TGAACAGCGT GCTTCCACGC TCTCCTGGCC CCTGTGGATG 1090       1100       1110       1120       1130       1140
GGGGTGCCCC ACGGCTACGA GATCGAGTTC ATCTTTGGGA TCCCCCTGGA CCCCTCTCGA
                                            ← ⊖
      1150       1160       1170       1180       1190       1200
AACTACACGG CAGAGGAGAA AATCTTCGCC CAGCGACTGA TGCGATACTG GGCCAACTTT
                                  GTCCCTGACT ACCCTAT 5'

1210       1220       1230       1240       1250       1260
GCCCGCACAG GGGATCCCAA TGAGCCCCGA GACCCCAAGG CCCCACAATG GCCCCCGTAC
ache
      1270       1280       1290       1300       1310       1320
ACGGCGGGGG CTCAGCAGTA CGTTAGTCTG GACCTGCGGC CGCTGGAGGT GCGGCGGGGG
                                                             ← ⊖
      1330       1340       1350       1360       1370       1380
CTGCGCGCCC AGGCCTGCGC CTTCTGGAAC CGCTTCCTCC CCAAATTGCT CAGCGCCACC
                                                     3' TCGCGGTCG 1390       1400       1410       1420       1430       1440
GACACGCTCG ACGAGGCGGA CCGCCAGTGG AAGGCCGAGT TCCACCGCTG GAGCTCGTAC
CTGTGCCAGC TGCTCCGCCT C 5'
                      ← ⊖
      1450       1460       1470       1480       1490       1500
ATGGTGCACT GGAAGAACCA GTTCGACCAC TACAGCAAGC AGGATCGCTG CTCAGACCTG
 3' TACTACGTGA CCTTCTTCGT CAACCTGGTG AT 5'

1510       1520       1530       1540       1550       1560
TGACCCCGGC GGGACCCCCA TGTCCTCCGC TCCGCCCGGC CCCCTAGCTG TATATACTAT 1570       1580       1590       1600       1610       1620
TTATTTCAGG GCTGGGCTAT AATACAGACA GACGAGCCCC AGACTCTGCC CGAATTCTAG
```

FIG. 1d

```
        1630       1640       1650       1660       1670       1680
   AGGTCCCCGG GTACCGAGCT CGCGAGCCCC AGACTCTGCC CATCCCCAGC CCACCCCGAC 1690       1700       1710       1720       1730       1740
   GTCCCCGGGG CTCCGGTCCT CTGGCATGTC TTCAGGCTGA GCTCCTCCCC GCGTGCCTTC 1750       1760       1770       1780       1790       1800
   GCCCTCTGGC TGCAAATAAA CTGTTACAGG CCAAAAAAAA AAAAAAAAAA AAAAAAAAAA

AAAAAA
```

FIG. 1e

```
         1  CCTCTCTCCCCTCATCTTTGCCAACCTGCCCCACCTCCTCTGCAGCTGAGCGATAACCCT
        61  TGGGCCGACAGTGCCCTAATCTCCTCCCTCCTGGCTTCTCGACCGACCCTTCACCCTTTC
       121  CCTTTCTTTCTCCCAGCAGACGCCGCCTGCCCTGCAGCCATGAGGCCCCCGCAGTGTCTG
                                                     Ⓜ                      7
       181  CTGCACACGCCTTCCCTGGCTTCCCCACTCCTTCTCCTCCTCCTCTGGCTCCTGGGTGGA
                                                                           27
       241  GGAGTGGGGCTGAGGGCCGGGAGGATGCAGAGCTGCTGGTGACGGTGCGTGGGGGCCGG
signal                                Ⓔ                                   47
peptide 301  CTGCGGGATTCGCCTGAAGACCCCGGGGGCCCTGTCTCTGCTTTCCTGGGCATCCCCTTT
                                                                           67
       361  GCGGAGCCACCCATGGGACCCCGTCGCTTTCTGCCACCGGAGCCCAAGCAGCCTTGGTCA
                                                                           87
       421  GGGGTGGTAGACGCTACAACCTTCCAGAGTGTCTGCTACCAATATGTGGACACCCTATAC
                                           Ⓒ                               107
       481  CCAGGTTTTGAGGGCACCGAGATGTGGAACCCCAACCGTGAGCTGAGCGAGGACTGCCTG
                                                              Ⓒ            127
       541  TACCTCAACGTGTGGACACCATACCCCCGGCCTACATCCCCCACCCCTGTCCTCGTCTGG
                                                                           147
       601  ATCTATGGGGGTGGCTTCTACAGTGGGGCCTCCTCCTTGGACGTGTACGATGGCCCGCTTC
K-153                                                                      167
       661  TTGGTACAGGCCGAGAGGACTGTGCTGGTGTCCATGAACTACCGGGTGGCAGCCTTTGGC
                                                                           187
       721  TTCCTGGCCCTGCCGGGGAGCCGAGAGGCCCCGGGCAATGTGGGTCTCCTGGATCAGAGG
                                                                           207
       781  CTGGCCCTGCAGTGGGTGCAGGAGAACGTGGCAGCCTTCGGGGGTGACCCGACATCAGTG
                                                                           227
       841  ACGCTGTTTGGGGAGAGCGCGGGAGCCGCCTCGGTGGGCATGCACCTGCTGTCCCCGCCC
OPSYNO                       Ⓢ                                             247
       901  AGCCGGGGCCTGTTCCACAGGGCCGTGCTGCAGAGCGGTGCCCCCAATGGACCCTGGGCC
                                                                           267
       961  ACGTGGGCATGGGACAGGCCCGTCGCAGGGCCACGCAGCTGGCCCACCTTGTGGGCTGT
                                                                    Ⓒ     287
      1021  CCTCCAGGCGGCACTGGTGGCAATGACACAGAGCTGGTAGCCTGCCTTCGGACACGACCA
                              ⓃⒹⓉ            Ⓒ                            307
      1081  GCGCAGGTCCTGGTGAACCACGAATGGCACGTGCTGCCCTCAAGAAAGCGTCTTCCGGTTC
                                                                           327
      1141  TCCTTCGTGCCCTGTGGTAGATGGAGACTTCCTCAGTGACACCCCAGAGGCCCTCATCAAC
                                                                           347
      1201  GCGGGAGACTTCCACGGCCTGCAGGTGCTGGTGGGTGTGGTGAAGGATGAGGGCTCGTAT
                                                                           367
      1261  TTTCTGGTTTACGGGGCCCCAGGCTTCAGCAAAGACAACGAGTCTCTCATCAGCCCGGCC
                                                 ⓃⒺⓈ                      387
      1321  GAGTTCCTGGCCGGGGTGCGGGTCGGGGTTCCCCAGGTAAGTGACCTGGCAGCCGAGGCT
```

FIG. 1f

```
                                                                              407
      1381  GTGGTCCTGCATTACACAGACTGGCTGCATCCCGAGGACCCGGCACGCCTGAGGGAGGCC
                                                                              427
      1441  CTGAGCGATGTGGTGGGCGACCACAATGTCGTGTGCCCCGTGGCCCAGCTGGCTGGGCGA
                                  ©                                           447
      1501  CTGGCTGCCCAGGGTGCCCGGGTCTACGCCTACGTCTTTGAACACCGTGCCTTCCACGCTC
                                                                              467
      1561  TCCTGGCCCCTGTGGATGGGGGTGCCCCACGGCTACGAGATCGAGTTCATCTTTGGGATC
                                                                              487
      1621  CCCCTGGACCCCTCTCGAAACTACACGGCAGAGGAGAAAATCTTCGCCCAGCGACTGATG
                                    (N  Y  T)                                 507
      1681  CGATACTGGGCCAACTTTGCCCGCACAGGGGATCCCAATGAGCCCCGAGACCCCAAGGCC
                                                                              527
      1741  CCACAATGGCCCCCGTACACGGCGGGGCTCAGCAGTACGTTAGTCTGGACCTGCGGCCG
                                                                              547
      1801  CTGGAGGTGCGGCGGGGGCTGCGCGCCCAGGCCTGCGCCTTCTGGAACCGCTTCCTCCCC
                                  ©                                           567
      1861  AAATTGCTCAGCGCCACCGACACGCTCGACGAGGCGGAGCGCCAGTGGAAGGCCGAGTTC
                                                                              587
      1921  CACCGCTGGAGCTCCTACATGGTGCACTGGAAGAACCAGTTCGACCACTACAGCAAGCAG
CTACHE                       _____         607
      1981  GATCGCTGCTCAGACCTGTGACCCCGGCGGGACCCCCATGTCGTCCGCTCCGCCCGGCCC
                        ©      Ⓛ                                              627
      2041  CCTAGCTGTATATACTATTTATTTCAGGGCTGGGCTATAACACAGACGAGCCCCAGACTC
      2101  TGCCCATCCCCACCCCACCCCGACGTCCCCGGGGCTCCCGGTCCTCTGGCATGTCTTCA
      2161  GGCTGAGCTCCTCCCCGCGTGCCTTCGCCCTCTGGCTGCAAATAAACTGTTACAGGCCAA
      2221  AAAAAAAAAAAAAAAAAAAAAAAAAAAAAAAA  2253
```

FIG. 1g

```
                                      30                                              60
ATG TGG AAC CCC AAC CGT GAG CTG AGC GAG GAC/TGC\CTG TAC CTC AAC GTG TGG ACA CCA
Met Trp Asn Pro Asn Arg Glu Leu Ser Glu Asp\Cys/Leu Tyr Leu Asn Val Trp Thr Pro 90                                             120
TAC CCC CGG CCT ACA TCC CCC ACC CCT GTC CTC GTC TGG ATC TAT GGG GGT GGC TTC TAC
Tyr Pro Arg Pro Thr Ser Pro Thr Pro Val Leu Val Trp Ile Tyr Gly Gly Gly Phe Tyr 130                                             190
AGT GGG GCC TCC TCC TTG GAC GTG TAC GAT GGC CGC TTC TTG GTA CAG GCC GAG ACC ACT
Ser Gly Ala Ser Ser Leu Asp Val Tyr Asp Gly Arg Phe Leu Val Gln Ala Glu Thr Thr 210                                             240
GTG CTG GTG TCC ATG AAC TAC CGG GTG GGA GCC TTT GGC TTC CTG GCC CTG CCG GGG AGC
Val Leu Val Ser Met Asn Tyr Arg Val Gly Ala Phe gly Phe Leu Ala Leu Pro Gly Ser 270                                             300
CGA GAG GCC CCG GGC AAT GTG GGT CTC CTG GAT CAG AGG CTG CCC CTG CAG TGG GTG CAG
Arg Glu Ala Pro Gly Asn Val Gly Leu Leu Asp Gln Arg Leu Ala Leu Gln Trp Val Gln 330       OPSYNO (334-362)                      360
GAG AAC GTG GCA GCC TTC GGG GGT GAC CCG ACA|TCA GTG ACG CTG TTT GGG GAG AGC CCG|
Glu Asn Val Ala Ala Phe Gly Gly Asp Pro Thr|Ser Val Thr Leu Phe Gly Glu Ser Ala|

390                                             420
|GG|A GCC GCC TCG GTG GGC ATG CAC CTG CTG TCC CCG CCC AGC CGG GGC CTG TTC CAC AGG
|Gl|y Ala Ala Ser Val Gly Met His Leu Leu Ser Pro Pro Ser Arg Gly Leu Phe His Arg 450                                             480
GCC GTG CTG CAG AGC GGT GCC CCC AAT GGA CCC TGG GCC ACG GTG GGC ATG GGA GAG GCC
Ala Val Leu Gln Ser Gly Ala Pro Asn Gly Pro Trp Ala Thr Val Gly Met Gly Glu Ala 510                                             540
CGT CGC AGG GCC ACG CAG CTG GCC CAC CTT GTG GGC/TGT\CCT CCA GGC GGC ACT GGT GGG
Arg Arg Arg Ala Thr Gln Leu Ala His Leu Val Gly\Cys/Pro Pro Gly Gly Thr Gly Gly 570                                             600
AAT GAC ACA GAG CTG GTA GCC/TGC\CTT CGG ACA CGA CCA GCG CAG GTC CTG GTG AAC CAC
Asn Asp Thr Glu Leu Val Ala\Cys/Leu Arg Thr Arg Pro Ala Gln Val Leu Val Asn His 630                                             660
GAA TGG CAC GTG CTG CCT CAA GAA AGC GTC TTC CGG TTC TCC TTC GTG CCT GTG GTA GAT
Glu Trp His Val leu Pro Gln Glu Ser Val Phe Arg Phe Ser Phe Val Pro Val Val Asp
```

FIG. 1h

```
                              690                                          720
GGA GAC TTC CTC AGT GAC ACC CCA GAG GCC CTC ATC AAC GCG GGA GAC TTC CAC GGC CTG
Gly Asp Phe Leu Ser Asp Thr Pro Glu Ala Leu Ile Asn Ala Gly Asp Phe His Gly Leu 750                                          780
CAG GTG CTG GTG GGT GTG GTG AAG GAT GAG GGC TCG TAT TTT CTG GTT TAC GGG GCC CCA
Gln Val Leu Val Gly Val Val Lys Asp Glu Gly Ser Tyr Phe Leu Val Tyr Gly Ala Pro 810                                          840
GGC TTC AGC AAA GAC AAC GAG TCT CTC ATC AGC CGG GCC GAG TTC CTG GCC GGG GTG CCG
Gly Phe Ser Lys Asp Asn Glu Ser Leu Ile Ser Arg Ala Glu Phe Leu Ala Gly Val Arg 870                                          900
GTC GGG GTT CCC CAG GTA AGT GAC CTG GCA GCC GAG GCT GTG GTC CTG CAT TAC ACA GAC
Val Gly Val Pro Gln Val Ser Asp Leu Ala Ala Glu Ala Val Val Leu His Tyr Thr Asp 930                                          960
TGG CTG CAT CCC GAG GAC CCG GCA CGC CTG AGG GAG GCC CTG AGC GAT GTG GTG GGC GAC
Trp Leu His Pro Glu Asp Pro Ala Arg Leu Arg Glu Ala Leu Ser Asp Val Val Gly Asp 990                                         1020
CAC AAT GTC GTG/TGC\CCC GTG GCC CAG CTG GCT GGG CAG ACT GGC/TGC\CCA GGG/TGC\CCG
His Asn Val Val\Cys/Pro Val Ala Gln Leu Ala Gly Gln Thr Gly\Cys/Pro Gly\Cys/Pro 1050                                         1080
GGT ACT ACG CCT AAC GTC TTT GAA CAC CGT GCT TCC ACG CTC TCC TGG CCC CTG TGG ATG
Gly Thr Thr Pro Asn Val Phe Glu His Arg Ala Ser Thr Leu Ser Trp Pro Leu Trp Met 1110                                         1140
GGG GTG CCC CAC GGC TAC GAG ATC GAG TTC ATC TTT GGG ATC CCC CTG GAC CCC TCT CGA
Gly Val Pro His Gly Tyr Glu Ile Glu Phe Ile Phe Gly Ile Pro Leu Asp Pro Ser Arg 1170                                         1200
AAC TAC ACG GCA GAG GAG AAA ATC TTC GCC CAG CGA CTG ATG CGA TAC TGG GCC AAC TTT
Asn Tyr Thr Ala Glu Glu Lys Ile Phe Ala Gln Arg Leu Met Arg Tyr Trp Ala Asn Phe 1230                                         1260
GCC CGC ACA GGG GAT CCC AAT GAG CCC CGA GAC CCC AAG GCC CCA CAA TGG CCC CCG TAC
Ala Arg Thr Gly Asp Pro Asn Glu Pro Arg Asp Pro Lys Ala Pro Gln Trp Pro Pro Tyr 1290                                         1320
ACG GCG GGG GCT CAG CAG TAC GTT AGT CTG GAC CTG CGG CCG CTG GAG GTG CGG CGG GGG
```

FIG. 1i

Thr Ala Gly Ala Gln Gln Tyr Val Ser Leu Asp leu Arg Pro Leu Glu Val Arg Arg Gly

```
                    1350                                        1380
CTG CGC GCC CAG GCC/TGC\GCC TTC TGG AAC CGC TTC CTC CCC AAA TTG CTC AGC GCC ACC
Leu Arg Ala Gln Ala\Cys/Ala Phe Trp Asn Arg Phe Leu Pro Lys Leu Leu Ser Ala Thr 1410                                        1440
GAC ACG CTC GAC GAG GCG GAG CGC CAG TGG AAG GCC GAG TTC CAC CGC TGG AGC TCC TAC
Asp Thr Leu Asp Glu Ala Glu Arg Gln Trp Lys Ala Glu Phe His Arg Trp Ser Ser Tyr
```

CTACTHE (1440-1472)

```
                                    1470                        1500
ATG GTG CAC TGG AAG AAC CAG TTC GAC CAC TAC AGC AAG CAG GAT CGC/TGC\TCA GAC CTG
Met Val His Trp Lys Asn Gln Phe Asp His Tyr Ser Lys Gln Asp Arg\Cys/Ser Asp Leu 1530                                        1560
TGA CCC CGG CGG GAC CCC CAT GTC CTC CGC TCC GCC CGG CCC CCT AGC TGT ATA TAC TAT 1590                                        1620
TTA TTT CAG GGC TGG GCT ATA ATA CAG ACA GAC GAG CCC CAG ACT CTG CCC GAA TTG GAC 1650                                        1680
AGG TCC CCG GGT ACC GAG CTC GCG AGC CCC AGA CTC TGC CCA TCC CCA CCC CAC CCC GAC 1710                                        1740
GTC CCC GGG GCT CCG GTC CTC TGG CAT GTC TTC AGG CTG AGC TCC TCC CCG CGT GCC TTC 1770                                        1800
GCC CTC TGG CTG CAA ATA AAC TGT TAC AGG CCA AAA AAA AAA AAA AAA AAA AAA AAA AAA
``` ache

AAA AAA

3 – UNTRANSLATED REGION

FIG. 1j

```
   1 CCTCTCTCCCCTCATCTTTGCCAACCTGCCCCACCTCCTCTGCAGCTGAGCCGATAACCCT
  61 TGGGCCGACAGTGCCCTAATCTCCTCCCTCCTGGCTTCTCGACCGACCCTTCACCCTTTC
 121 CCTTTCTTTCTCCCAGCAGACGCCGCCTGCCCTGCAGCCATGAGGCCCCCGCAGTGTCTG
                                           Ⓜ  R  P  P  Q  C  L    7
 181 CTCCACACGCCTTCCCTGGCTTCCCCACTCCTTCTCCTCCTCCTCTGGCTCCTCGGTGGA
      L  H  T  P  S  L  A  S  P  L  L  L  L  L  L  W  L  L  G  G   27
 241 GGAGTGGGGGCTGAGGGCCGGGAGGATGCAGAGCTGCTGGTGACGGTGCGTGGGGGCCGG
      G  V  G  A  E  G  R  Ⓒ  D  A  E  L  L  V  T  V  R  G  G  R   47
 301 CTGCGGGATTCGCCTGAAGACCCCGGGGGCCCTGTCTCTGCTTTCCTGGGCATCCCCTTT
      L  R  D  S  P  E  D  P  G  G  P  V  S  A  F  L  G  I  P  F   67
 361 GCGGAGCCACCCATGGGACCCCGTCGCTTTCTGCCACCGGAGCCCAAGCAGCCTTGGTCA
      A  E  P  P  M  G  P  R  R  F  L  P  P  E  P  K  Q  P  W  S   87
 421 GGGGTGGTAGACGCTACAACCTTCCAGAGTGTCTGCTACCAATATGTGGACACCCTATAC
      G  V  V  D  A  T  T  F  Q  S  V  Ⓒ  Y  Q  Y  V  D  T  L  Y  107
 481 CCAGGTTTTGAGGGCACCGAGATGTGGAACCCCAACCGTGAGCTGAGCGAGGACTGCCTG
      P  G  F  E  G  T  E  M  W  N  P  N  R  E  L  S  E  D  Ⓒ  L  127
 541 TACCTCAACGTGTGGACACCATACCCCCGGCCTACATCCCCCACCCCTGTCCTCGTCTGG
      Y  L  N  V  W  T  P  Y  P  R  P  T  S  P  T  P  V  L  V  W  147
 601 ATCTATGGGGGTGGCTTCTACAGTGGGGCCTCCTCCTTGGACGTGTACGATGGCCGCTTC
      I  Y  G  G  G  F  Y  S  G  A  S  S  L  D  V  Y  D  G  R  F  167
 661 TTGGTACAGGCCGAGAGGACTGTGCTGGTGTCCATGAACTACCGGGTGGGAGCCTTTGGC
      L  V  Q  A  E  R  T  V  L  V  S  M  N  Y  R  V  G  A  F  G  187
 721 TTCCTGGCCCTGCCGGGGAGCCGAGAGGCCCCGGGCAATGTGGGTCTCCTGGATCAGAGG
      F  L  A  L  P  G  S  R  E  A  P  G  N  V  G  L  L  D  Q  R  207
 781 CTGGCCCTGCAGTGGGTGCAGGAGAACGTGGCAGCCTTCGGGGGTGACCCGACATCAGTG
      L  A  L  Q  W  V  Q  E  N  V  A  A  F  G  G  D  P  T  S  V  227
 841 ACGCTGTTTGGGGAGAGCGCGGGAGCCGCCTCGGTGGGCATGCACCTGCTGTCCCCGCCC
      T  L  F  G  E  Ⓢ  A  G  A  A  S  V  G  M  H  L  L  S  P  P  247
 901 AGCCGGGGCCTGTTCCACAGGGCCGTGCTGCAGAGCGGTGCCCCCAATGGACCCTGGGCC
      S  R  G  L  F  H  R  A  V  L  Q  S  G  A  P  N  G  P  W  A  267
 961 ACGGTGGGCATGGGAGAGGCCCGTCGCAGGGCCACGCAGCTGGCCCACCTTGTGGGCTGT
      T  V  G  M  G  E  A  R  R  R  A  T  Q  L  A  H  L  V  G  Ⓒ  287
1021 CCTCCAGGCGGCACTGGTGGGAATGACACAGAGCTGGTAGCCTGCCTTCGGACACGACCA
      P  P  G  G  T  G  G  Ⓝ Ⓓ Ⓣ E  L  V  A  Ⓒ  L  R  T  R  P  307
1081 GCGCAGGTCCTGGTGAACCACGAATGGCACGTGCTGCCTCAAGAAAGCGTCTTCCGGTTC
      A  Q  V  L  V  N  H  E  W  H  V  L  P  Q  E  S  V  F  R  F  327
1141 TCCTTCGTGCCTGTGGTAGATGGAGACTTCCTCAGTGACACCCCAGAGGCCCTCATCAAC
      S  F  V  P  V  V  D  G  D  F  L  S  D  T  P  E  A  L  I  N  347
1201 GCGGGAGACTTCCACGGCCTGCAGGTGCTGGTGGGTGTGGTGAAGGATGAGGGCTCGTAT
      A  G  D  F  H  G  L  Q  V  L  V  G  V  V  K  D  E  G  S  Y  367
1261 TTTCTGGTTTACGGGGCCCCAGGCTTCAGCAAAGACAACGAGTCTCTCATCAGCCGGGCC
      F  L  V  Y  G  A  P  G  F  S  K  D  Ⓝ Ⓔ Ⓢ L  I  S  R  A  387
1321 GAGTTCCTGGCCGGGGTGCGGGTCGGGGTTCCCCAGGTAAGTGACCTGGCAGCCGAGGCT
      E  F  L  A  G  V  R  V  G  V  P  Q  V  S  D  L  A  A  E  A  407
```

FIG. 1k

```
1381  GTGGTCCTGCATTACACAGACTGGCTGCATCCCGAGGACCCGGCACGCCTGAGGGAGGCC
       V  V  L  H  Y  T  D  W  L  H  P  E  D  P  A  R  L  R  E  A    427
1441  CTGAGCGATGTGGTGGGCGACCACAATGTCGTGTGCCCCGTGGCCCAGCTGGCTGGGCGA
       L  S  D  V  V  G  D  H  N  V  V  ©  P  V  A  Q  L  A  G  R    447
1501  CTGGCTGCCCAGGGTGCCCGGGTCTACGCCTACGTCTTTGAACACCGTGCTTCCACGCTC
       L  A  A  Q  G  A  R  V  Y  A  Y  V  F  E  H  R  A  S  T  L    467
1561  TCCTGGCCC TGTGGATGGGGGTGCCCCACGGCTACGAGATCGAGTTCATCTTTGGGATC
       S  W  P  L  W  M  G  V  P  H  G  Y  E  I  E  F  I  F  G  I    487
1621  CCCCTGGACCCCTCTCGAAACTACACGGCAGAGGAGAAAATCTTCGCCCAGCGACTGATG
       P  L  D  P  S  R (N  Y  T) A  E  E  K  I  F  A  Q  R  L  M    507
1681  CGATACTGGGCCAACTTTGCCCGCACAGGGGATCCCAATGAGCCCCGAGACCCCAAGGCC
       R  Y  W  A  N  F  A  R  T  G  D  P  N  E  P  R  D  P  K  A    527
1741  CCACAATGGCCCCCGTACACGGCGGGGGCTCAGCAGTACGTTAGTCTGGACCTGCGGCCG
       P  Q  W  P  P  Y  T  A  G  A  Q  Q  Y  V  S  L  D  L  R  P    547
1801  CTGGAGGTGCGGCGGGGGCTGCGCGCCCAGGCCTGCGCCTTCTGGAACCGCTTCCTCCCC
       L  E  V  R  R  G  L  R  A  Q  A  ©  A  F  W  N  R  F  L  P    567
1861  AAATTGCTCAGCGCCACCGACACGCTCGACGAGGCGGAGCGCCAGTGGAAGGCCGAGTTC
       K  L  L  S  A  T  D  T  L  D  E  A  E  R  Q  W  K  A  E  F    587
1921  CACCGCTGGAGCTCCTACATGGTGCACTGGAAGAACCAGTTCGACCACTACAGCAAGCAG
       H  R  W  S  S  Y  M  V  H  W  K  N  Q  F  D  H  Y  S  K  Q    607
1981  GATCGCTGCTCAGACCTGTGACCCCGGCGGGACCCCCATGTCCTCCGCTCCGCCCGGCCC
       D  R  ©  S  D  L  *                                            627
2041  CCTAGCTGTATATACTATTTATTTCAGGGCTGGGCTATAACACAGACGAGCCCCAGACTC
2101  TGCCCATCCCCACCCCACCCCGACGTCCCCCGGGGCTCCCGGTCCTCTGGCATGTCTTCA
2161  GGCTGAGCTCCTCCCCGCGTGCCTTCGCCCTCTGGCTGCAAATAAACTGTTACAGGCCAA
2221  AAAAAAAAAAAAAAAAAAAAAAAAAAAAAAAA  2253
```

FIG. 1L

AMINO ACID SEQUENCES OF HUMAN ACETYLCHOLINESTERASE AND
BUTYRYLCHOLINESTERASE AS COMPARED WITH BOVINE, DROSOPHILA MELANOGASTER
AND TORPEDO CALIFORNICA ACETYLCHOLINESTERASE AND WITH BOVINE
THYROGLOBULIN AND ESTERASE 6 FROM DROSOPHILA

```
H.AChE     MRPPQCLLHTPSLA-------SPLLLLLLWLLGGGVGAEGREDAE--LLVTVRGGRLRDSPED-PGGPVSA
H.BuChE    -------------MHSKVTI----ICIRFLFWFVLLCMLIGKSHTEDDIIIATKNGKVRGMNLTVFGGTVTA
B.AChE     -------------------------------EGPEDPE---LLVMVRGGELRGLRLMAPRGPVSA
T.AChE     ---------MNLLVT------SSLGVLLHLVVLC--QADDHSK--LLVNTKSGKVMGTRVPVLSSHISA
D.AChE     MAISCRQSRVLPMSLPLPLTIPLPLVLVLSLHLSG--VCGVIDR---LVVQTSSGPVRGRSVTVQCREVHV
D.Est 6    ------------M-NYVGL----GLIIVL-SCLWL--GSNASDTDDPLLYQLPQGKLAG------RDNGSYYS
Bov.Tg.    ----------------------------------------VPI---ATHCQLLGRSQAIQVGTSWKPVDQ

H.AChE     FLGIPFAEPPMGPRRFLPP--EPKQPWSGVVDATTFQSVCYQYVDTLYPGFEGTEMWNPNRELSEDCLYLN

H.BuChE    FLGIPYAQPPLGRLRFKKP-QSLTKWSDIWNATKYANSCCQNIDQSFPGFHGSEMWNPNTDLSEDCLYLN

B.AChE     FLGIPYAEPPVGPRRFLPP-EPKRPWPGVLNATAFQSVCYQYVDTLYPGFEGTEMWNPNRELSEDCLYLN

T.AChE     FLGIPFAEPPVGNMRFRRP-EPKKPWSGVWNASTYPNNCQQYVDEQFPGFSGSEMWNPNREMSEDCLYLN

D.AChE     YTGIPYAKPPVEDLRFRKP-VPAEPWHGVLDATGLSATCVQERYEYFPGFSGEEIWNPNTNVSEDCLYIN

D.Est 6    YESIPYAEPPTGDLRFEAPEPYKQKNSDIFDATKTPVAGLQ-WDQFTPG--------AN-KLVGEEDCLTVS

Bov.Tg.    FLGVPYAAPPLGEKRFRAP-EHL-NWTGSWEATKPRARC-------WQPGIRTP-----TPPGVSEDCLYLN

H.AChE     VWTP-YPRPTSTPP-----------------------------VLVWIYGGGFYSGASSLDVYDGR
H.BuChE    VWIP-APKP-KNAT-----------------------------VLIWIYGGGFQTGTSSLHVYDGR
B.AChE     VWTP-YPRP-SSPT-----------------------------VLVGIYGGGFYSGASSLDVYDGR
T.AChE     IWVP-SAPR-PKSTT----------------------------VMVWIYGGGFYSGSSTLDVYNGK
D.AChE     VWAP-AKAR-LRHGRGANGGEHPNGKQADTDHLIHNGNPQNTTNGLPILIWIYGGGFMTGSATLDIYNAD
D.Est 6    VYKPKNSKR-NSFP-----------------------------VVAHIHGGAFMFG--AAWQNGHE
Bov.Tg     VFVP-QNMA-PNAS-----------------------------VLVFFHNAAEGKGSGDRPAVDGS

H.AChE     FLVQAETTVLVSMNYRVGAFGFLALPGS--------REAPGNVGLLDQRLALQWVQENVAAFGGDPTSVTLF
H.BuChE    FLARVERVIVVSMNYRVGALGFLALPGN--------PEAPGNMGLFDQQLALQWVQKNIAAFGGNPKSVTLF
B.AChE     FLVQAEGTVLVSMNYRVGAPGFLALPGS--------REAPGNYGLLDQRLALQSVQENVAAFGGDPTSVTLF
T.AChE     YLAYTEEVVLVSLSYRVGAFGFLALHGS--------QEAPGNVGLLDQRMALQWVRDNIQFFGGDPKTVTIF
D.AChE     IMAAVGNVIVASFQYRVGAFGFLMLAPEMPSEFAEEAPGNVGLWDQALALRWLKDNAHAFGGNPEWMTLF
D.Est 6    NVMREGKFILVKISYRLGPLGF-VSTGD--------RDLPGNYGLKDQRLALKWIKQNIASFGGEPQNVLLV
Nov.Tg     FLAYTGNLIVVTASYRTGIFGFLS-SGS--------SELSGNWGLLDQVVALTWVQTHIQAFGGDPRRVTLA
```

FIG. 2

```
H.AChE    GESAGAASVGMHLL--SPPSRGLFHRAVLQSGAPNGPWATVGMGEARRRATQLAHLVGCPPGG-TGGNDT

H.BuChE   GESAGAASVSLHLL--SPGSHSLFTRAILQSGSFNAPWAVTSLYEARNRTLNLAKLTGC------SRENET

B.AChE    GESAGAASVGMHFX--SPGSRXXXXXAVLQSGAPNGPNATVGVGEAQYVYVELLNPXXX------XXXXXX

T.AChE    GESAGGASVGMHIL--SPGSRDLFRRAILQSGSPNCPWASVSVAEGRRRAVELGRNLNC------NLNSDE

D.AChE    GESAGSSSVNAQLM--SPVTRGLVKRGMMQSGTMNAPWSHMTSEKAVEIGKALINDCNC------NASMLK

D.Est 6   GHSAGGASVHLQML--REDFGQL-ARA-AFSFSGNALDPWVIQKGARGRAFELGRNVGC------ESAEDST

Bov.Tg    ADRGGADIASIHLVTTRAANSRLFRRAVLMGGSALSPAAVIRPERARQQAAALAKEVGC------PSSSVQ

H.AChE    ELVACLRTRPAQVLVNHEWHVLPQESVFRFSF--VPVVDGDFLSDTPEALINAGDFHGLQVLVGVVKDEG

H.BuChE   EIIKCLRNKDPQEILLNEAFVVPYGTPLSVNF--GPTVDGDFLTDMPDILLELGQFKKTQILVGVNKDEG

B.AChE    XMVHCLKARPAQDLVDMEWRVLPQEHVFRFSF--VPVIDGEFFPXXXEXXXXXGQFKKTQPALVPAKDEG

T.AChE    ELIHCLREKKPQELIDVEWNVLPFDSIFRFSF--VPVIDGEFFPTSLESMLNSGNFKKTQILLGVNRDEG

D.AChE    TNPAHVMSCMRSVDAKTISVQQMNSYSGILSFPSAPTIDGAFLPADPMTLMKTAQLKDYDILMGNVRDEG

D.Est 6   SLKKCLKSKPASE--LVTA-VRKFLIFSYVPF--APFSPVLEPSDAPD--AIITQDPRDVIRSGKFGQVP

Bov.Tg    EMVSCLRQEPARILNDAQTKLLAVSGPFH-YW--GPVVDGQYLRETPARVLQRAPRVKVDLLIGSSQDDG

H.AChE    SYFLVYGAPG-FSKDNESLISRAEFLAGVRVGVPQ-VSDLA-AEAVVLHYTDWLHPEDPARL-REALSDV
H.BuChE   TAFLVYGAPG-FSKDNNSIITRKEFQEGLKIFFPG-VSEFG-KESILFHYTDWVDDQRPENY-REALGQV
B.AChE    SYFLVYGAPG-FSDXXXXXIARGNFXXXXXKVGVPQ-ASDLA-AEAVVLHYTDWLHPEDPARX-XEALSDV
T.AChE    SFFLLYGAPG-FSKDSESKISREDFMSGVKLSVPH-ANDLG-LDAVTLQYTDWMDDNNGIKN-RDGLDDI
D.AChE    TYFLLYDFIDYFDKDDATALPRDKYLEIMNNIFGK-ATQAE-REAIIFQYTSWEG-NPGYQN-QQQIGRA
D.Est 6   WAVSYVTEDG------GYNAALLLKERKSGIVIDDLN-ERWLE-LAPYLLFYRDTKTKKDMDDYSRKIKQEY
Bov.Tg    LINRAKAVKQ-FEESQCRTSSKTAFYQALQNSLGGEAADAGVQAAATWYYSLEHDSDDYASF-SRALEQA

H.AChE    VGDHNV-VCPVAQLAGRTGCPGCPGTTPNVFEHRASTLSWPLWMGVPHGYEIEFTFGIPL---DPSRNYTA

H.BuChE   VGDYNF-ICPALEFTKKFSEWGNNAFFYY-FEHRSSKLPWPEWMGVMHGYEIEFVFGLPL---ERRDNYTK
```

FIG. 2a

```
B.AChE    VGDHNV-VCPVAQLAGRXXXXXXXXVYAYI-FEHRASTLSWPEWMGVPHGYEIEFIFGLPL---EPSLNYTI
T.AChE    VGDHNV-ICPLMHFVNKYTKFGNGIYLYF-FNHRASNLVWPEWMGVIHGYEIEFVFGLPL---VKELNYTA
D.AChE    VGDHFF-TCPTNEYAQALAERGASVHYYY-FTHRTSTSLWGEWMGVLHGDEIEYFFGQPL---NNSLQYRP
D.Est 6   IGNQQFDIESYSELQRLF------TDILFKN-STQES--LDLHRKYGKSPAY--AYVYDNPA--EKGIAQVL
Bov.Tg    TRDYFI-ICPVIDMA---SHWARTVRGNV-FMYHAPESYSHSSLELL---TDVLYAFGLPKYPAYEGQFTL

H.AChE    E-EKIFAQRLMRYWANFARTGDPNEPRDPKAPQWPPYTAGAQQYVSLDLRPLEV--------RRGLRAQA-C
H.BuChE   A-EEILSRSIVKRWANFAKYGNPNETQNNSTS-WPVFKSTEQKYLTLNTESTR--------IMTKLRAQQC
B.AChE    E-ERTFAQRLMRYWANFARTGDPNDPRKAKQP-WPLYTTKXXXXXXX-XXXXKV--------PQASLAQA-C
T.AChE    E-EFALSRRIMHYWATFAKTGNPNEPHSQESK-WPLFTTKEQKFIDLNTEPMK--------VHQHLRVQMC
D.AChE    V-ERELGKRMLSAVIEFAKTGNPAQDGEE----WPNFSKEDPVYYIFSTDDKIEKL----ARGPLAAR-C
D.Est 6   ANRTDYDFGTVHGDDYFLIFENFVRDVEMRPDEQIISRNFINMLADF-ASS----------DNGSLKYGEC
Bov.Tg    E-EKSLSLKQMQYFSNFIRSGNPNYPHEFSRRAPEFAAPWPDFVPRDGAESYKELSVLLPNRQGLKKADC

H.AChE    AFWNR-FLPKLLSATDTLDEAERQWKAEFHRWSSYMVHWKNQF-DHY-SKQDRCSDL    583
H.BuChE   RFWTS-FFPKVLEMTGNIDEAEWEWKAGFHRWNNYMMDWKNQF-NDYTSKKESCVGL    574
B.AChE    AFWNR-FLPKLRNATDTLDEAERQWKAEFHRWSSYMVHWKNQF-DHY-SKQDRCSDL    574
T.AChE    -VWNQ-FLPKLLNATETIDEAERQWKTEFHRWSSYMMHWKNQF-DHY-SRHESCAEL    575
D.AChE    -SWND-YLPKVRSWAGTCDGDSGSASISPRLQLLGIAALIYICAALRTKRVF----
D.Est 6   DFKDSVGSEKFQLLAIYIDAARIGSMWNF-RKLHE----------------------
Bov.Tg    SFWSK-YIQSLKASADETKDGPSADSEEEDQPAGSGLTEDLLGLPELASKTYSK --   2750
```

FIG. 2b

ACTIVE SITE HOMOLOGIES

| | |
|---|---|
| Hu. BuChE | NPKSV—TLFGESAGAASVSLHL |
| Hu. AChE | DPTSV—TLFGESAGAASVGMHL |
| Tor. AChE | DPKTV—TIFGESAGGASVGMHI |
| Dros. AChE | NPEWM—TLFGESAGSSSVNAQL |
| | |
| Dros. Est 6 | EPENV—LLVGHSAGGASVHLEM |
| Pig Elastase | -GNGVRSGCQGDSGGPLV—CQK |
| Bov. Chymotrypsin | -ASGV-SSCQGDSGGPLV—CQK |
| Bov. Prothrombin | EGK-RGDACEGDSGGPFVMKSPY |
| Bov. Factor X | DTQPE-DACQGDSGGPHV—TRF |
| Hu. Plasminogen | G—T—DSCQGDSGGPLV—CFE |
| α lytic Protease | IQTNV-CAEPGDSGGSL |

| Active Site Homology of HuAChE to: | Overall Homology of HuAChE to: |
|---|---|
| Hu. BuChE − 85% | Hu. BuChE: 51% |
| Tor. AChE   78% | Tor. AChE   56% |
| Dros. AChE  52% | Dros. AChE  31% |

FIG.3

GENETICALLY ENGINEERED HUMAN ACETYLCHOLINESTERASE

This invention was made with support by the U.S. Army Medical Research and Development Command under Contract No. DAMD 17-87 C 7169 to Hermona Soreq. The U.S. Army has certain rights in the invention.

This is a continuation of application Ser. No. 07/496,554, filed Mar. 20, 1990, now abandoned.

FIELD OF THE INVENTION

The invention relates to genetically engineered human acetylcholinesterase. The invention is also directed to the cloning and production of human acetylcholinesterase. The invention is further directed to the production of antibodies interacting with said protein. The invention also relates to pharmaceutical compositions comprising acetylcholinesterase for treatment and prophylaxis of organo-phosphorous compounds poisoning. The compositions of the present invention may also be used to relieve post-surgery apnea. Methods of treating or preventing organophosphorous poisoning or post-operative apnea by employing the pharmaceutical compositions of the invention are also within the scope of the application. The invention further relates to human cholinesterase probes which may be employed for diagnosing progressing ovarian carcinomas and hemocytopoietic disorders. Methods of diagnosing such tumors or hemocytopoietic disorders are also envisaged within this application. Furthermore, methods of treating hemocytopoietic disorders are also considered.

Throughout this application, various publications are referenced by Arabic numerals within parentheses. Full citations for these references may be found at the end of the specifition immediately preceding the claims. The disclosures of these publications in their entireties are hereby incorporated by reference into this application in order to more fully describe the state of the art as known to those skilled therein as of the date of the invention described and claimed herein.

BACKGROUND OF THE INVENTION

Properties of Cholinesterases

Cholinesterases (ChEs) are highly polymorphic carboxylesterases of broad substrate specificity, involved in the termination of neurotransmission in cholinergic synapses and neuromuscular junctions. ChEs terminate the electrophysiological response to the neurotransmitter acetycholine (ACh) by degrading it very rapidly (1). ChEs belong to the B type carboxylesterases on the basis of their sensitivity to inhibition by organophosphorous (OP) poisons (2) and are primarily classified according to their substrate specificity and sensitivity to selective inhibitors into acetylcholinesterase (ACHE, acetylcholine acetylhydrolase, EC 3.1.1.7) and butyrylcholinesterase (BuChE, acylcholine acylhydrolase, EC 3.1.1.8) (3). Further classifications of ChEs are based on their charge, hydrophobicity, interaction with membrane or extracellular structures and multisubunit association of catalytic and non-catalytic "tail" subunits (4,5).

The severe clinical symptoms resulting from OP intoxication (6) are generally attributed to their inhibitory interaction on AChE (7). OPs are substrate analogues to ChEs. The labeled OP diisopropylfluorophosphate (DFP) was shown to bind convalently to the serine residue at the active esteratic site region of ChEs, that is common to all of the carboxyl-esterases (8,9). However, the binding and inactivation capacity of OPs on ChEs is considerably higher than their effect on other serine hydrolases. Furthermore, even within species the inhibition of ChEs by different OPs tends to be highly specific to particular ChE types (10). In order to improve the designing of therapeutic and/or prophylactic drugs to OP intoxication, it was therefore desirable to reveal the primary amino acid sequence and three dimensional structure of human ACHE, and to compare them to those of human BuChE, as well as to the homologous domains in other serine hydrolases.

AChE may be distinguished from the closely related enzyme BuChE by its high substrate specificity and sensitivity to selective inhibitors (11). Both enzymes exist in parallel arrays of multiple molecular forms, composed of different numbers of catalytic and non-catalytic subunits (12). However, in humans, as in other species, they display a tissue-specific mode of expression. BuChE, assumed to be produced in the liver, is the principal species in serum (13). In contrast, AChE is the major cholinesterease in various human brain regions (14), including the cholinoceptive basal brain ganglia (15).

Extensive research efforts by several groups resulted in recent years in the isolation of cDNA clones encoding the electric fish AChE (16,17), Drosophila AChE (18,19) and human BuChE (20,21). However, the primary structure of mammalian, and more particularly, human AChE remained unknown.

Interaction of Cholinesterases with Organophosphorous Insecticides and War Gases The use of organophosphorous (OP) anticholinesterase compounds in war (22) and as agricultural insecticides (23) resulted, over the last 40 years, in an interesting number of cases of acute and delayed intoxication. These included damage to the peripheral and central nervous system, myopathy, psychosis, general paralysis and death (24). Estimations are that 19,000 deaths occur out of the 500,000 to 1 million annual pesticide-associated poisonings (25). Previous animal studies demonstrated that methyl parathion administration suppressed growth and induced ossification in both mice and rats, as well as high mortality and cleft palate in the mouse (26). In humans, malformations of the extremities and fetal death were correlated with exposure to methyl parathion in 18 cases (27). In addition, a neonatal lethal syndrome of multiple malformations was reported in women exposed to unspecific insecticides during early pregnancy (28).

Complete inhibition of ChEs by the administration of OP poisons is lethal (6). This inhibition is achieved by formation of a stable stoichiometric (1:1) covalent conjugate with the active site serine (7), followed by a parallel competing reaction, termed "aging", which transforms the inhibited ChE into a form that cannot be generated by the commonly used reactivators (7) such as active-site directed nucleophiles (e.g., quaternary oximes) which detach the phosphoryl moiety from the hydroxyl group of the active site serine (70). The aging process is believed to involve dealkylation of the covalently bound OP group (7), and renders therapy of intoxication by certain organophosphates such as Sarin, DFP and Soman, exceedingly difficult (29).

Use of preparations comprising ChEs for therapeutical purposes has been demonstrated to be effective at laboratory level: purified AChE from fetal calf serum has been shown to protect rats from 2 lethal doses of Soman (a war OP poison) with half life of 5–6 days (37,38). Purified BuChE from human serum has been shown to improve the symptoms of OP-intoxicated patients (31).

Interaction of Cholinesterases with Succinylcholine—Post-Operative Apnea

Succinylcholine which acts as a competitive analogue of acetylcholine, is often used in surgery as a short-term muscle relaxant. Since the drug is hydrolyzed by BuChE, its administration into individuals carrying genetically abnormal BuChE causes prolonged apnea (32). The most common variant with this problem is the atypical variant $E^s$, for which 3–6% of the Caucasian population is heterozygous and about 0.05% is homozygous (33). This enzyme hydrolyzes acetylcholine but not succinylcholine (34). Another variant, $E^1$, which causes the complete absence of catalytically active serum BuChE in homozygotes, is also associated with this clinical problem (35). This type of "silent" enzyme cannot hydrolyze any ChE substrate, nor can it bind organophosphate compounds (9). High frequency of atypical and silent BuChE genes was reported among Iraqui and Iranian Jews (11.3% for heterozygotes and 0.08% for homozygotes, respectively) (36–38). This could explain the high frequency of reports of prolonged apnea following surgery in Israel, and apparently in many other countries. It is likely that AChE could be administered to patients to rid the body of the succinylcholine in cases of prolonged apnea.

Alterations in the Level and Properties of Cholinesterases

In several neurological or genetic disorders, such as Senile Dementia of the Alzheimer's type or Down's syndrome, modification in both the level (39) and the composition of molecular forms (40) of human brain acetylcholinesterase have been reported. In the Alzheimer's disease, the levels of AChE in cholinergic brain areas drops by about 50% and the tetrameric form of the enzyme dissappears completely. Individuals with Down's syndrome invariably develop manifestations of the Alzheimer's disease before the age of 40. In addition, it has been observed that neural tube defects in human embryos are clinically characterized by secretion of AChE tetramers into the amniotic fluid. These phenomenae are currently tested for by sucrose gradient fractionation, followed by enzymatic assays of substrate hydrolysis or gel electrophoresis and AChE activity staining. Simple and selective quantitative assays for specific AChE forms have not yet been developed.

Furthermore, death at very early stages of development has been observed in Homozygote *Drosophila* mutants lacking the Ace locus which controls AChE biosynthesis and in nematode mutants defective in the expression of their four ChE genes. It is very likely that homozygous mutations in AChE genes in humans will result in early abortion or in severe neurological and possibly other malformations in the fetus. No methods to determine whether specific individuals carry such mutations have been disclosed so far.

Relationship between Cholinesterases and Hematopoiesis and Blood Cells Differentiation Biochemical and histochemical analyses indicate that both acetylcholinesterase and butyrylcholinesterase are expressed in high levels in various fetal tissues of multiple eukaryotic organisms (41), where ChE are coordinately regulated with respect to cell proliferation and differentiation (42). However, no specific role could be attributed to ChE in embryonic development and their biological function(s) in these tissues remained essentially unknown (71).

In addition to its presence in the membrane of mature erythrocytes, AChE is also intensively produced in developing blood cells in vivo (43) and in vitro (44) and its activity serves as an accepted marker for developing mouse megakaryocytes (45). Furthermore, administration of acetylcholine analogues as well as ChE inhibitors has been shown to induce megakaryocytopoiesis and increased platelet counts in the mouse (46), implicating this enzyme in the commitment and development of these hematopoietic cells.

Recently, the cDNA coding for BuChE has been cloned (20) and BuChEcDNA hybridizing sequences have been localized to chromosome sites 3q21,26 and 16q12 (47). It is of importance to emphasize that the chromosome 3q21,26 region includes breakpoints that were repeatedly observed in peripheral blood chromosomes of patients with acute myelodisplastic leukemia (AML) (48,49). These cases all featured enhanced megakaryocytopoiesis, high platelet count and rapid progress of the disease (15). Accumulating evidence in recent reports implicates chromosomal breakpoints with molecular changes in the structure of DNA and the induction of malignancies (51). Therefore, the connection between: (a) abnormal control of megakaryocytopoiesis in AML as well as in mouse bone-marrow cells subjected to ChE inhibition; (b) cholinesterase genes location on the long arm of chromosome 3; and (c) chromosomal aberrations in that same region in AML, appeared more than coincidental (for discussion see (47)).

The putative correlation between the human genes coding for ChEs and the regulation of megakaryocytopoiesis has been examined by searching for structural changes in the human AChE and ChE genes from peripheral blood DNA in patients with leukemia, platelet count abnormalities, or both. Proof of the active role of these enzymes in the progress of human hematopoiesis had to be established.

Relationship between Cholinesterases and Ovarian Carcinomas

High level of expression of AChE and ChE in tumors was reported in the past (66,67), however, it was still to be elucidated whether this high expression level is effected by gene amplification. The rapidly progressing carcinomas of the ovary (68) may offer a promising model in which to test said possibility since sections from these tumors exhibit pronounced diffuse cytochemical staining of ChE activities (66), whereas ChE expression in normal ovarian tissue appears to be confined to maturing oocytes (47).

The possible amplification of the human AChE and ChE genes in primary ovarian carcinomas, and their expression in dividing cells within tumor loci, implicating involvement of cholinesterase in tumor growth and development, had to be established.

SUMMARY OF THE INVENTION

The invention is directed to human acetylcholinesterase, a neurotransmitter hydrolyzing enzyme, which has a major role in the termination of neurotransmission in cholinergic synapses and neuromuscular junctions. The invention provides for a molecule, as well as DNA and mRNA sequences which code for human acetylcholinesterase. Sources for large scale production of human acetylcholinesterase may be prepared by genetic engineering.

The invention therefore provides a molecule encoding human acetylcholinesterase. Contrary to previous expectations it was found that the gene encoding acetylcholinesterase is completely not homologous to the previously isolated gene encoding the related enzyme butyrylcholinesterase, notwithstanding the apparent similarity between these two proteins. This non-obvious finding distinguishes the probes of the present invention from those of near inventions in this field. The invention also provides genetic sequences encoding human acetylcholinesterase or biologically active essential fragments thereof or polypeptides having human acetylcholinesterase activity. Expression vectors containing such molecule or genetic sequences are also provided, as well as hosts transformed with the expression vectors, and methods of producing the genetically engineered human acetylcholinesterase or biologically active essential fragments thereof or the polypeptides having human acetylcholinesterase activity.

Human acetylcholinesterase or the biologically active essential fragments thereof or the polypeptides having human acetylcholinesterase activity, produced by the methods of the invention are useful in the treatment of organophosphorous poisoning, as an antidote for the treatment of patients suffering from such organophosphorous intoxication, and also in the prophylaxis of such poisonings. Additionally, the acetylcholinesterase of the present invention, or the biologically active essential fragments thereof or the polypeptides having human acetylcholinesterase activity, may be useful in relieving post-surgery apnea, resulting from prior administration of succinylcholine. Thus, the invention relates to pharmaceutical compositions comprising as active ingredient human acetylcholinesterase or biologically active essential fragments thereof or the polypeptides having human acetylcholinesterase activity, produced by the methods of the invention and to methods of treating or preventing organophosphorous poisoning or post-surgery apnea.

The human acetylocholinesterase or its biologically active fragments or the polypeptides having human acetylcholinesterase activity produced by the methods of the invention can also be used to elicit antibodies raised thereagainst. These antibodies, which specifically interact with said protein or polypeptides, may be used for the detection of disease-related changes of acetylcholinesterase in patients. Assays for detecting the presence or absence of acetylcholinesterase altered by a disease or congenital disorder in a patient are also provided.

Furthermore, fragments of cDNAs encoding for cholinesterases, for example cDNA of human acetylocholinesterase, may be suitably labeled and used as probes in hybridizaton tests for the detection of alterations in the respective cholinesterase genes. Such alterations appear in patients suffering from leukemia, platelet count abnormalities and possibly other blood cells disorders. Additionally, such alterations have been shown to also appear in patients with primary ovarian, and possibly other, carcinomas. The invention thus provides methods of diagnosing the above pathological conditions. Therapeutic compositions for, and methods of treating said pathological conditions, employing cDNA sequences encoding for human cholinesterases or fragments thereof may also be contemplated. Specific oligonucleotide preparations based on said cDNA sequence may be used as "antisense" compounds, aimed at blocking the expression of said genes in leukemic patients, providing a novel chemotherapeutic approach based on the early diagnosis of a previously unclassified syndrome.

DESCRIPTION OF THE FIGURES

FIGS. 1c–1e shows the cDNA sequence of clones BGSA and FL2B, encoding for fetal human ACHE, with the oligonucleotides referred to in FIG. 1a marked by boxes.

FIGS. 1f–1g shows the composite DNA sequence of the clones presented in FIG. 1c, encoding for the complete human ACHE, with some of the oligonucleotides referred to in FIG. 1b overlined.

FIGS. 1h, 1i, 1j show the primary structure of fetal human AChE encoded by the cDNA given in FIGS. 1c, 1d, 1e.

FIGS. 1k, 1l shows the primary structure of the full-length human AChE encoded by the cDNA sequence given in FIGS. 1f, 1g.

FIGS. 2, 2a, 2b shows amino acid sequences of human AChE and BuChE as compared with *Drosophila melanogaster*, bovine and *Torpedo californica* AChEs and with bovine thyroglobulin and Esterase 6 from *Drosophila*.

FIG. 3 shows a comparison of ChE active site region sequences with other serine hydrolases. The star indicates [$^3$H]-DFP-labeled or active site serine.

DETAILED DESCRIPTION OF THE INVENTION

Figure 1A:
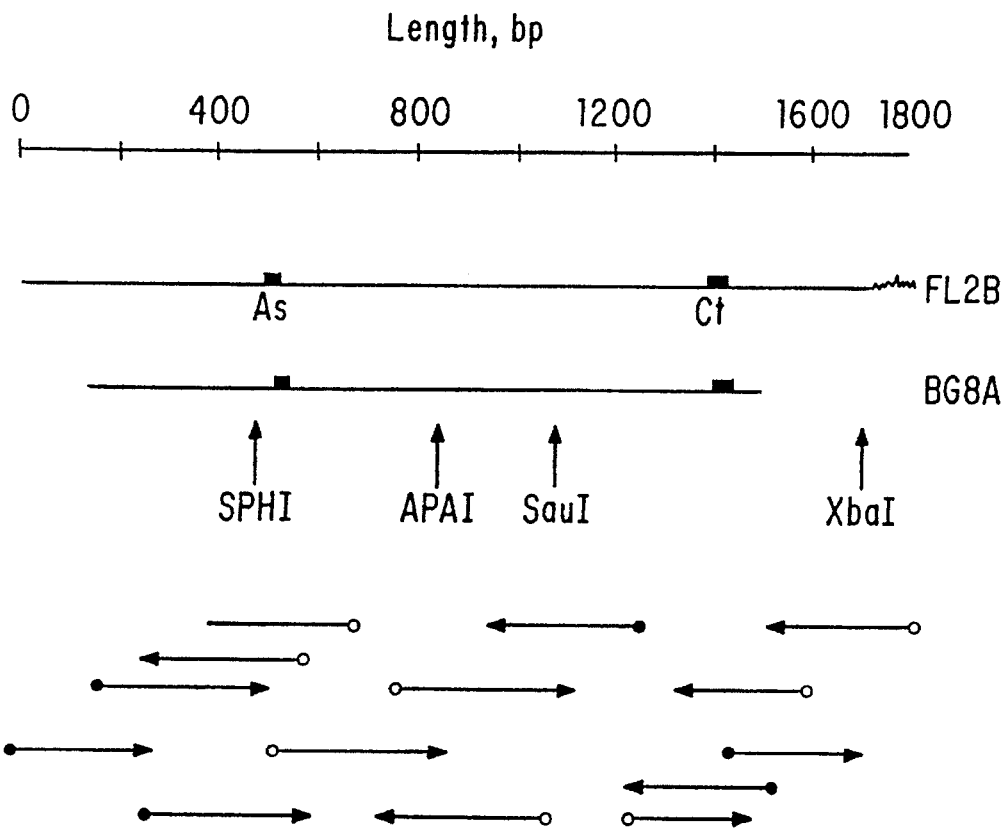
FIG. 1a shows the sequencing strategy for AChEcDNA clones BG8A and FL2B from newborn brain basal nuclei and fetal liver and brain.

The human acetylcholinesterase, its biologocally active essential fragments or the polypeptides having acetylcholinesterase activity of the invention may be prepared by cloning the cDNA encoding the protein or polypeptide and expressing the cloned DNA sequence.

cDNA encoding human acetylcholinesterase or its said fragments or said polypeptides may be derived from various tissues. Brain cells, and particularly cells from adult brain basal ganglia, that are highly enriched with cholinoceptive cell bodies, may be preferred. The cDNA may be cloned, and the resulting clone screened with an appropriate probe for the cDNA coding for the desired sequence.

Further, the gene of human acetylcholinesterase may be synthesized according to techniques known in the art and cloned for use in preparing the active enzyme in large scale and for producing antibodies thereagainst.

The cloned cDNA may then be inserted into appropriate expression vector(s) to be transfected into heterologous cells. In the present case eukaryotic cells, possibly of embryonic or nervous system origin, may be preferable as hosts. Alternatively, non-mammalian cells such as microinjected *Xenopus* oocytes or yeast may be employed to produce the authentic recombinant AChE protein.

The expressed protein may be isolated and purified in accordance with conventional methods such as extraction, precipitation, chromatography, affinity chromatography, electrophoresis, or the like.

The recombinant acetylcholinesterase or its said fragments or said polypeptides produced according to the method of the invention, may be used as active ingredients in pharmaceutical compositions for the prophylaxis or treatment of organophosphorus poisoning. Pharmaceutical compositions of the invention may also be used to relieve post-surgery apnea resulting from administration of succinylcholine. The pharmaceutical compositions of the invention may also contain pharmaceutically acceptable carriers and diluents, which are well known in the art. In view of the high Kd value of AChE to OP's (16) it promises to be far more efficient for both said applications than other therapeutic agents, mostly aimed to prevent the "aging" process (i.e. oximes) or to improve the dynamic equilibrium between the neurotransmitter, receptor and enzyme by partially blocking the receptor (i.e., atropine). Moreover, being a human authentic protein it is expected, under normal circumstances not to induce toxic or immunological complications, and may therefore be highly advantageous over the currently available drugs such as oximes and atropin. In the case of prolonged apnea, it can save considerable intensive care expenses and (in some cases) brain damage and even death. AChE is the original target for both OP agents (particularly war ones) and succinylcholine, and as such, it carries the best-adapted binding sites for both types of agents. It is a highly stable protein, that will be available in large quantities and may be stored for prolonged periods, and due to its high stability it also promises to be effective in relatively small doses and for a long time (days).

The invention also enables to clinically detect cholinesterase deficiencies or abnormalities in the cholinesterase genes, by using oligonucleotide hybridization to a patient's genomic DNA. Such detection techniques are known in the art, for example, the detection of abnormalities in the gene coding for sickle cell β-s globin (52). Detection of such abnormalities may be of importance in preventing post-surgery apnea, described above. In addition, it may be of marked importance in diagnosing various leukemias and abnormal megakaryocytopoiesis for which significant correlation between the disease and cholinesterases genes has now been found. It may be mentioned that treatment of such blood disorders by employing direct derivatives of recombinant cholinesterases is envisaged within the scope of the present invention. The invention thus provides for assays adapted to distinguish between normal and defective sequences in minute samples of the genomic DNA and in a single hybridization step.

Specific antibodies may be elicited against the acetylcholinesterase, or biologically active essential fragments thereof. These antibodies may be used, for example by radioimmunoassay, to rapidly and simply detect poisoning or disease related changes in cholinesterases.

Preliminary observations which will be described in the following EXAMPLES, show that mutations in the ChE gene(s) are found in patients suffering various blood disorders and also in certain individuals exposed to chronic doses of parathion, which is a potent precursor of the cholinesterase inhibitor paraoxon. The defective genes can be identified for diagnostic purposes and also at very early gestational stage, by hybridization, by using DNA from patients or from chronic villi or amniotic fibroblasts and well-characterized probes from AChE and/or ChE gene(s).

Further recent observations which will also be described in the following EXAMPLES, show that the genes coding for the AChE and ChE enzymes are intensively expressed in multiple types of tumor tissues, including ovarian carcinomas. As will be shown hereafter, presence of translatable AChEmRNA and ChEmRNA, as well as their active protein products, was revealed in discrete tumor foci. The frequent co-amplification in these tumors of AChE and ChE genes implicates cholinesterases with neoplastic growth and/or proliferation. The defective genes can be identified by the techniques mentioned above, and this identification may be of considerable diagnostic value, enabling treatment at very early stages of the disease.

The invention thus further provides an assay for the determination in mammals, including humans, of genetically altered cholinesterase-producing genes, essentially comprising the steps of: (a) obtaining DNA samples from the patient; (b) enzymatically restricting the DNA; (c) electrophoretically separating fragments of the DNA and blotting the fragments on a suitable support; (d) providing a labeled DNA or RNA probe of pre-determined sequence from cholinesterase or essential fragments thereof or polypeptides having human cholinesterase activity; (e) hybridizing the fragments obtained by step (c) with the probe (d); and (f) detecting the presence or absence of altered genes according to the hybridization pattern.

The invention will now be described in more detail on hand of the following EXAMPLES, which are illustrative and do not limit the invention unless otherwise specified.

EXAMPLES

Example 1

General Methods

To search for cDNA clones encoding human ACHE, oligodeoxynucleotide probes were synthesized according to the amino acid sequences in evolutionarily conserved and divergent peptides from electric fish AChE (17) as compared with human serum BuChE (53,20,9). These synthetic oligodeoxynucleotide probes were used for a comparative screening of cDNA libraries from several human tissue origins.

Previous biochemical analyses revealed that in the fetal human brain, the ratio AChE:BuChE is close to 20:1 (14) In contrast, the cDNA library from fetal human liver was found to be relatively rich in BuChEcDNA clones (20). Therefore, cDNA clones were searched for, that would interact with selective oligodeoxynucleotide probes, designed according to AChE-specific peptide sequences in cDNA libraries from fetal and adult brain origin, and particularly from brain basal ganglia that are highly enriched with cholinoceptive cell bodies. Positive clones were then examined for their relative abundance in brain-originated cDNA libraries, as compared with liver. Brain-enriched cDNAs were further tested for their capacity to hybridize with the OPSYN oligodeoxynucleotide probes, previously designed according to the concensus amino acid sequence at the active esteratic site of ChEs (53). Finally, the confirmed clones were hybridized with BuChEcDNA and found to be not homologous to it.

Use of Oligodeoxynucleotides in Hybridization Reactions and Isolation of cDNA Clones In detail, differential screening of various cDNA libraries from fetal human tissues was performed using two different oligodeoxynucleotide probes, designed to complement the predicted mRNA sequence as follows. Probe CTACHE, d[3'- ATG.TAC.TAC.GTG.ACC.TTC.TTG.GT-C.AAG.CTG-GTG-AT], a 35-mer that represents the peptide sequence Tyr-Met-Met-His-Trp-Lys-Asn-Gln-Phe-Asp-His-Tyr, present in the c'-terminal region of *Torpedo* AChE (17), and in which G or C residues were inserted in positions where codon ambiguity presented a choice between G or T or between C or A, respectively. This probe was designed so that it would not hybridize with BuChE, since 3 out of the 12 amino acids are different in the parallel peptide of human BuChE (20). Probe OPSYNO, d[3'-AA.CCI.CT(CorT-).(TC(A or G).AGI)CGI.CCI. CGI.CGI.(TC(A or G).AGI).CA], a 29-mer with a 36-fold degeneracy in which deoxyinosine was inserted in positions where codon ambiguity permits all four nucleotides (20), and where only one or the other of the two triplets in parentheses is present. This probe was expected to hybridize with both BuChEcDNA and AChEcDNA since it codes for the peptide Phe-Gly-Glu-Ser-Ala-Gly-Ala-Ala-Ser-Val found in the active esteratic site of human serum BuChE and that differs from the parallel peptide of *Torpedo* AChE by one amino acid only (No. 7 in this peptide, Gly in *Torpedo*). Oligodeoxynucleotides were 5'-end-labeled and screening was performed as previously described (53,20), using cDNA libraries from basal brain nuclei of 1 day old newborn (donated to the American Type Culture Collection by R. A. Lazzarini) and from fetal liver [21 weeks gestation (20)]. Two clones with 1.5 Kb inserts from the basal nuclei library, later found to be identical, were found positive first with the selective and then with the common active site probe and were designated BGSA (FIG. 1a refers) and ABGACHE (FIG. 1aa refers). Rescreening of the basal nuclei and the fetal liver libraries with [$^{32}$P]-labeled BG8AcDNA resulted in the isolation of 40 and 19 positive clones, respectively, and DNA sequencing revealed that they all encoded polypeptides having the same active site sequence. One of the liver clones, designated FL2B (FIG. 1a) and another from fetal muscle, designated FEMA-CHE (FIG. 1aa) were found to also include complete 3'-non-translated regions of 500 bp, ended with a polyadenylation site and a poly(A) tail.

To reveal the full length of the AChE coding sequence, probe k-153, a 17-mer d[5'-CG°GCC°ATC°GTA°CAC°GTC], was designed according to the nucleotide sequence at the 5'-end of clone ABGACHE. It is complementary to the sequence encoding the peptide Asp-Val-Tyr-Asp-Gly-Arg that is highly specific for ACHE, and was used to screen a human genomic DNA library (BRL, Gaithersburg). The resultant genomic DNA clones were further characterized by hybridization with ABGACHEcDNA followed by double-strand DNA sequencing with the Sequenase kit (USB, Ohio). One of these clones, GNACHE, included the complete 5'-region of the AChE coding sequence, which was ligated with the cDNA clone to construct a pGEM transcription vector having the SP$_6$ RNA polymerase binding site (Promega, Madison). Transcription in vitro of this construct, *Xenopus* oocyte microinjection and acetylthiocholine hydrolysis were performed as recently described (77). Spontaneous substrate hydrolysis values were subtracted. The authentic nature of the recombinant AChE produced in the oocytes provided proof that this was indeed the correct sequence.

Example 2

Sequencing the AChEcDNA Clones

A. Sequencing strategy (i) The differential screening procedure described in Example 1 preliminarily resulted in the isolation of several brain, muscle and liver cDNA clones that included the regions complementary to probes CTACHE and OPSYNO (FIG. 1a) and which corresponded exactly to the peptide sequences used to design these oligodeoxynucleotide probes [FIG. 1c, FIG. 1d, FIG. 1e, amino acid residues encoded by nucleotides CTACHE (1440–1472) and OPSYNO (334–362), respectively]. All of the isolated clones contained large overlapping identical fragments, suggesting that they were derived from similar mRNA trancripts. Rescreening of cDNA libraries using these clones as probes further resulted in the isolation and characterization of fetal brain and liver cDNAs encoding the 3'-region of these cDNAs. A 400 nucleotide sequence from the 5'-region of AChEcDNA remained apparently missing because of the G,C-rich nature of this sequence, preventing reverse transcriptase from completing its synthesis.

According to the strategy schematically illustrated in FIG. 1a, the entire DNA inserts of BG8A and FL2B and their restriction endonuclease EcoRI fragments were isolated and subcloned in the sequencing vectors M13mP18, M13mP19 and pUC118 (Amersham, Stratagene). DNA sequencing of the resulting recombinants was done by the dideoxynucleaside procedure, using the universal 17-mer primer (Amersham, No. 4511, indicated by filled circles at the beginning of arrows) or unique 17-mer primers synthesized from confirmed cDNA sequences (indicated by arrows beginning with empty circles). Confirmed sequences were obtained from both strands of the cDNA as indicated by arrow length and direction. Sequence data were managed as detailed previously (5). Restriction sites for several nucleases were located by computer analysis of the sequence data and confirmed experimentally.

(ii) Further experiments of the differential screening described above resulted in the isolation of several additional brain, muscle and liver cDNA clones that included regions complementary to probes CTACHE and OPSYNO (FIG. 1b) and which correspond exactly to the peptide sequences used to design these oligodeoxynucleotide probes [FIG. 1f, FIG. g amino acid residues encoded by nucleotides CTACHE (1939–1947) and OPSYNO (847–876), respectively]. All of the isolated clones contained large overlapping identical fragments, suggesting that they were derived from similar mRNA trancripts and they were all terminated downstream of the region encoding the persued N-terminus of the AChE protein. A genomic DNA clone overlapping this region was then isolated which included the missing upstream sequence preceded by an AUG codon that was embedded in an appropriate concensus sequence for initiation of translation (21).

According to the strategy schematically illustrated in FIG. 1aa, the entire DNA inserts of ABGACHE, FEMACHE and GNACHE and their restriction endonuclease EcoRI fragments were isolated and subcloned in the sequencing vectors M13mP18, M13mP19 and pUC118 (Amersham, Stratagene). DNA sequencing of the resulting recombinants was done by the dideoxynucleaside procedure, using the universal 17-mer primer (Amersham, No. 4511, indicated by filled rectangles at the beginning of arrows) or unique 17-mer primers synthesized from confirmed cDNA sequences (indicated by arrows beginning with circles). Confirmed sequences were obtained from both strands of the cDNA as indicated by arrow length and direction. Sequence data were managed as detailed previously (5). Restriction sites for several nucleases were located by computer analysis of the sequence data and confirmed experimentally.

B. Primary structure of the fetal human AChE encoded by the brain and liver cDNA clones BG8A, F12B and FB5.

Figure 1B:
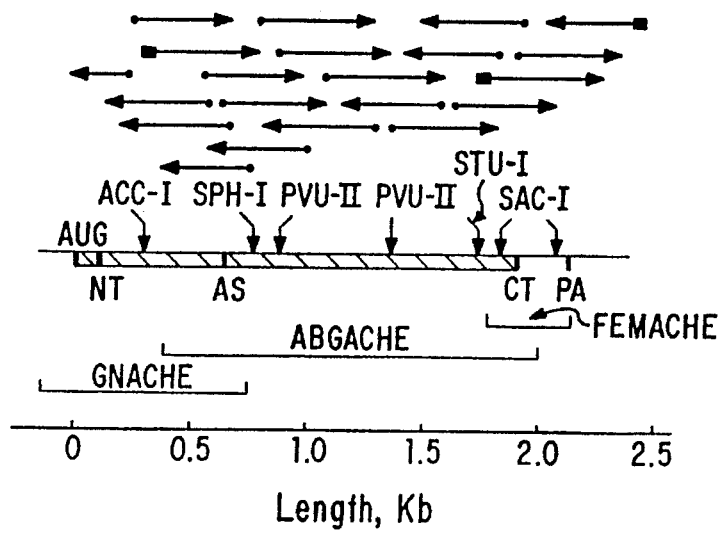
FIG. 1b shows the sequencing strategy for AChEcDNA clones ABGACHE and FEMACHE from adult brain basal nuclei and fetal muscle and the GNACHE genomic clone.

(i) As may be seen in FIG. 1b, FIG. 1i, the 1.8-Kb composite nucleotide sequence of clones BG8A and FL2B was translated into its encoded amino acid sequence. Nucleotides are numbered in the 5'-to-3' direction, and the predicted amino acids are shown below the corresponding nucleotide sequence. Boxing indicates the esteratic site 14 amino acid residues that was found to exactly match the parallel peptide present in human serum BuChE (14,15) and was encoded, as expected, by the synthetic OPSYNO concensus oligodeoxynucleotide probe. Also boxed is the c-terminal selective 12 amino acid residues sequence which matched with a single nucloetide mismatch the ACh-specific probe CTACHE (see Example 1) and which was expected and found to be completely different from the parallel peptide in BuChE. Three putative sites for potential N-linked glycosylation, predicted by the sequence AsnXaa-Thr/Ser, in which Xaa represents any amino acid except proline (14), are doubly underlined. Eight Cys residues are enclosed in hexagons. 3' untranslated region is marked. The primary structure of the various oligonucleotide probes used to sequence fetal human AChE is shown in FIG. 1c–1e.

(ii) In subsequent experiments, as may be seen in FIG. 1f–1g, the 2.2-Kb composite nucleotide sequence of clones GNACHE, ABGACHE and FEMACHE was translated into its encoded amino acid sequence. Nucleotides are numbered in the 5'-to-3' direction, and the predicted amino acids are shown below the corresponding nucleotide sequence. Overlining indicates the esteratic site 14 amino acid residues that was found to exactly match the parallel peptide present in human serum BuChE (14,15) and was encoded, as expected, by the synthetic OPSYNO concensus oligodeoxynucleotide probe. Also overlined is the c-terminal selective 12 amino acid residues sequence which matched with a single nucloetide mismatch (notched) the ACh-specific probe CTACHE (see Example 1) and which was expected and found to be completely different from the parallel peptide in BuChE. Three putative sites for potential N-linked glycosylation, predicted by the sequence AsnXaa-Thr/Ser, in which Xaa represents any amino acid except proline (14), are ovally circled. Nine Cys residues, as well as the first and last amino acids in the mature protein and the initiator methionine, are enclosed in circles. 5' and 3' untranslated regions are marked by no space between lines. The primary structure of the various oligonucleotide probes used to sequence fetal human AChE is shown in FIGS. 1f–1g.

Example 3

Expression of Cloned Composite ACbEDNA in Microinjected *Xenopus* Oocytes

In experiments for proving the identity and authenticity of the cloned AChEcDNA, the expression of its biologically active protein product was analyzed in *Xenopus* oocytes microinjected with synthetic AChEmRNA. For expression studies, consecutive DNA fragments from clones ABGACHE and GNACHE (FIG. 1aa) were prepared by digestion with the restriction enzymes Hind III and Sph I, ligated and subcloned into the pGEM-7ZF (Promega) transcription vector, linearized with EcoRI. EcoRI was heat inactivated (15 min, 68° C.) in both DNA samples and ligation was performed overnight at 4° C., in a reaction mixture containing 1 mM ATP, ligase buffer (according to the instructions of New England Biolabs) and 800 units of $T_4$ DNA ligase from the same source (NEB). Ligated DNA constructs were used to transform competent *E. coli* MV 1190 cells. Recombinant clones were detected by creating white colonies in the presence of IPTG and x-gal, indicating the inactivation of their β-galactosidase gene. Plasmid DNA was prepared from these colonies and employed for transcription in vitro using $T_3$ and $T_7$ RNA polymerase and cap analogue (Pharmacia). Synthetic mRNA transcripts were injected into *Xenopus* oocytes and AChE biosynthesis analyzed as previously detailed (77) for BuChEmRNA expression.

One ng. samples of full-length recombinant AChEmRNA transcribed from this construct (in three independent transcription experiments) reproducibly induced in microinjected *Xenopus* oocytes the biosynthesis of catalytically active AChE capable of hydrolyzing 0.3±0.05 nmol of acetylthiocholine per hr., about 1000-fold higher efficiency as compared with the production of AChE from poly(A)$^+$ brain mRNA (61). In contrast, the recombinant enzyme appeared to be much less (50-fold less) efficient in its ability to hydrolyze butyrylthiocholine. Furthermore, the oocyte-produced enzyme was markedly (100%) sensitive to inhibition by $10^{-5}$M of the selective AChE inhibitor 1,5-bis-(4-allyldimethylammoniumphenyl)-pentan-3-one dibromide (BW284C51) but totally insensitive to $10^{-5}$M of the selective organophosphorous BuChE inhibitor tetraisopropylpyrophosphoramide (iso-OMPA) in the same concentration (Table I). Altogether, these experiments demonstrated that the combined sequence encoded for authentic human ACHE.

TABLE I

Inhibition of Recombinant Human AChE Produced by Microinjected Xenopus Oocytes by Cholinesterase Inhibitors

| Inhibitor | AcThCho degraded pmol/hr per ng mRNA | % remaining activity |
| --- | --- | --- |
| 1. None | 300 ± 5 | 100 |
| 2. BW284C51 | 3 ± 1 | 1 ± 0.3 |
| 3. iso-OMPA | 280 ± 10 | 98 ± 3 | a. Microinjection was performed using synthetic mRNA encoding AChE from 3 separate in vitro transcription reactions. Total AChE-mediated hydrolysis of acetylthiocholine (AcThCho, 1 mM) as a substarte was determined spectrophotometrically within oocyte homogenates over a period of 8–10 hrs. from 3 separate microinjection experiments repeated in quadruplicate per assay.

b. In order to ascertain sensitivity to inhibitors, either BW284C51 (10 μM) or iso-OMPA (10 μM) were added to reaction mixtures 40 min. prior to the addition of the substrate. Net activities and percent inhibition values of recombinant AChE enzyme are shown, following subtraction of the endogenous AChE residing within *Xenopus* oocytes. Data shown represent mean values ±SEM.

Example 4

Amino Acid Homologies Between ChEases from Different Origins

When the amino acids predicted from the above cDNA sequences were aligned with the available complete sequence data published for human BuChE (20), *Torpedo* AChE (17) and *Drosophila* AChE (18) and esterase 6 (19) and with the incomplete sequence of bovine AChE and thyroglobulin (55), the entire coding region for a highly homologous protein was defined. This sequence includes the concensus active site which contains a serine residue that can be labeled by diisopropylfluorophosphate (FIGS. 2, 2a, 2b, indicated by a star).

The pronounced homology at the N-terminal part that is considerably higher between cholinesterases as compared with the esterase 6 and the thyroglobulin sequences should be noted.

The general amino acid composition of the protein encoded by these cDNAs was very similar to that reported for human erythrocyte AChE (56).

Example 5

A. Comparison of ChEs Active Site Region Sequences with other Serine Hydrolases

Active site region sequences of ChE were compared with those of other serine hydrolases. Results are shown in FIG. 3, in which the star indicates [$^3$H]-DFP-labeled or active site serine.

DNA sequence analysis followed by computerized alignment of the encoded primary amino acid sequences of human AChE and BuChE demonstrated, as expected, that the functional similarity among ChEs reflects genetic relatedness. The active site peptide of human ACHE, as deduced from the AChEcDNA clones, revealed 17 out of 21 amino acid residues identical to those of either human BuChE or *Torpedo* AChE (FIG. 3). Lower level of similarity (12 out of 21 amino acid residues) was observed in comparison with *Drosophila* AChE (18). Esterase 6 from *Drosophila* (19) displayed 10 identical residues out of these 21, and several serine preoteases—3 or 4 identical residues only (FIGS. 2, 2a, 2b). This comparison draws a distinct line between serine proteases and the family of carboxylesterases, and more particularly—the highly conserved ChEs.

B. Comparison of the Coding Region in Human AChEcDNA and the Inferred Amino Acid Sequence of the Human AChE Protein with the Parallel Sequences of other ChEs.

Figure 4:
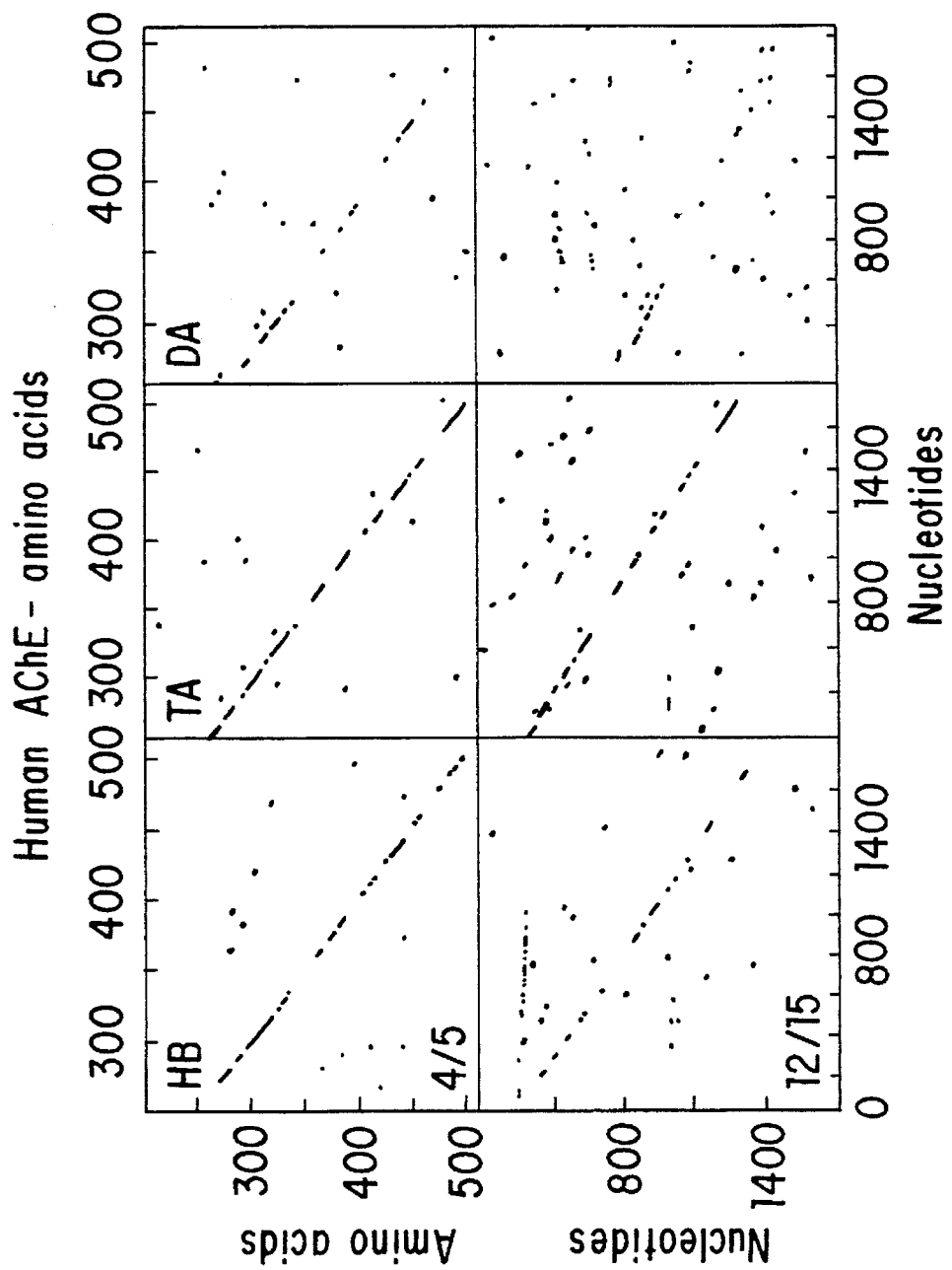
FIG. 4 shows amino acids (up) and nucleotide (down) similarities between the coding regions in most of the human AChEcDNA sequence and parallel regions in the cDNAs encoding for human BuChE (HB), *Torpedo* AChE (TA) and *Drosophila* AChE (DA).

The coding region in human AChEcDNA and the inferred amino acid sequence of the human AChE protein were compared with the parallel sequences of human BuCh-EcDNA (53,20,21), of AChEcDNA from *Torpedo* (17) and of the more evolutionarily remote AChEcDNA from *Drosophila* (18). Results are shown in FIG. 4. Regions of homology were searched for by the dot matrix approach (57). Match values that yielded clear homology regions and minimal background noise are presented: 12 out of 15 conservative matches for nucleotide sequence and 4 out of 5 conservative matches for amino acid residues. Nucleotides are numbered in the 5'-to-3' direction and amino acids in the N-to-C' direction for all of the sequences.

This analysis revealed several peptide regions and DNA sequence domains that are highly conserved in all of the ChEs and displayed clearly the higher level of divergence between human and *Drosophila* AChEs, as opposed to the extensive similarities between human AChE and BuChE and *Torpedo* ACHE. A higher level of conservation was found at the amino acid level (FIG. 4, up) than at the nucleotide level (FIG. 4, down) in complete agreement with previous observations (20,5). Significant homology was also observed with the DNA and the amino acid sequence of bovine thyroglobulin, in corroboration of previous findings (17,5). Notwithstanding this homology, the AChEcDNA sequence does not hybridize at all with the previously isolated BuChEcDNA. This is due to its G,C-rich nature, opposing the A,T-rich nature of BuChEcDNA.

C. Hydrophobicity Analysis of Human AChE and other ChE

Figure 5:
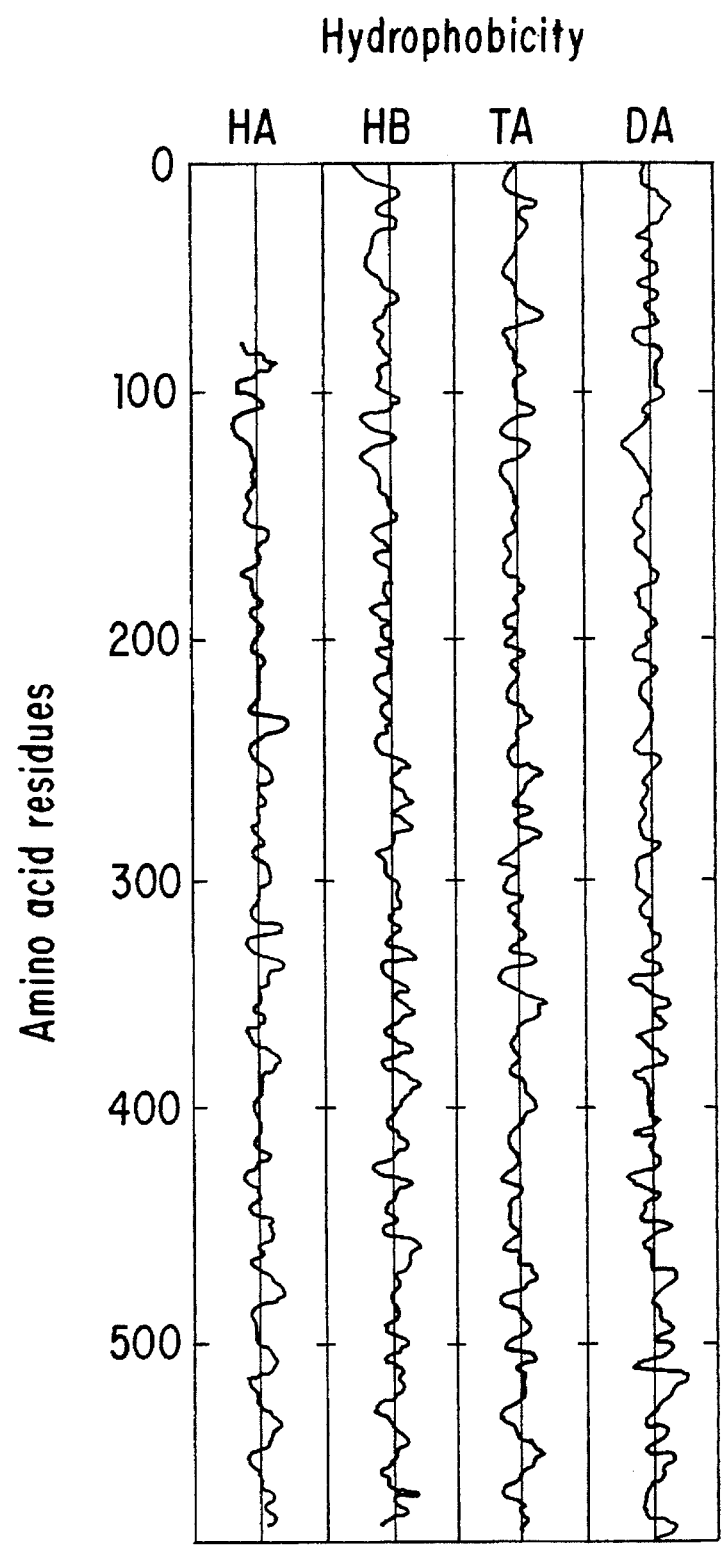
FIG. 5 shows comparative hydrophobicity patterns of members of the ChE family, human AChE (HA), human BuChE (HB), *Torpedo* AChE (TA) and *Drosophila* AChE (DA).
Figure 6A:
FIG. 6 shows the pronounced synthesis of ACHE, but not BuChE, mRNA transcripts in human fetal brain basal nuclei revealed by in situ hybridization with [$^{35}$S]-labeled ChEcDNA probes.
Figure 6B:
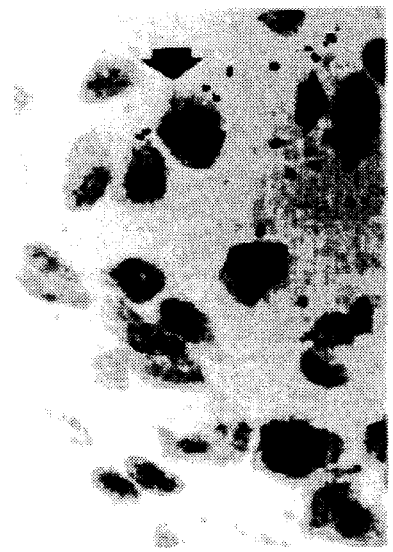
Figure 6C:
Figure 6D:
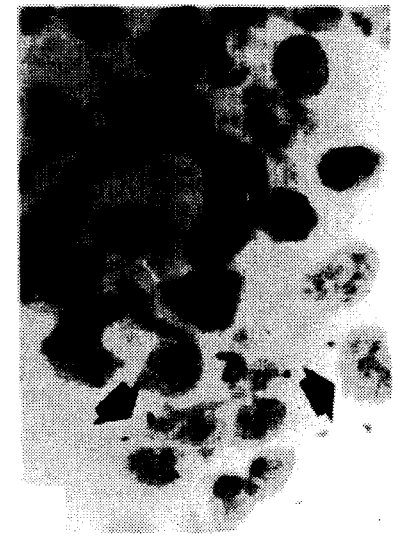

To further examine the molecular properties of the human AChE protein encoded by the newly isolated cDNA clones, it was subjected to hydrophobicity analysis according to (58). The results of this analysis are presented in FIG. 5, together with parallel analyses of the homologous sequences of human BuChE, *Torpedo* AChE and *Drosophila* ACHE. In FIG. 5, the dotted vertical baseline in each box represents a hydrophylicity value of —o—; increasing hydrophylicity is in the right-hand direction and increased hydrophobicity is in the left-hand direction.

The human AChE inferred from this sequence has three potential sites for asparagine-linked carbohydrate chains, less sites than *Torpedo* AChE (17) and human BuChE (20,21). Its hydropathy index and putative charge relay system, as well as lack of sequence homology to serine proteases distinguish this protein as a type B carboxy-lesterase of the cholinesterases family (8) with a c-terminal peptide that is characteristic of the soluble AChE forms (16,17). It includes 9 cysteine residues, as compared with 7 residues for *Torpedo* AChE (17) and with 8 for human BuChE (20,21). Six intrachain disulfide bonds would be predicted to be at $Cys^{68}$-$Cys^{95}$, $Cys^{256}$-$Cys^{271}$ and $Cys^{408}$-$Cys^{529}$. A fourth predicted disulfide bridge involves $Cys^{580}$ which, in all soluble cholinesterases, appears to be covalently attached to the parallel cysteine residue of an identical catalytic subunit (16,17). This leaves two additional cysteine residues at positions 419 and 422, that are particular to human ACHE.

Comparative analysis of the amino acid sequence inferred for human ACHE, human BuChE, *Torpedo* and *Drosophila* ACHE, *Drosophila* esterase 6 and bovine thyroglobulin revealed 5 clear domains of sequence similarities with a decreasing homology, and with higher sequence conservation at the N-terminal part of cholinesterease. Conserved cysteine residues appeared at the borders of these homologous domains, in parallel with a similar phenomenon in the insulin receptor protein family. The level of conservation at the amino acid level was found to be considerably higher than at the nucleotide level for all of these sequences.

Example 6

Pronounced Synthesis of AChEmRNA Transcripts in Human Fetal Brain Basal Nuclei

Human AChEcDNA and BuChEcDNA probes were purified by enzymatic restriction, agarose gel electrophoresis and electroelution and were labeled with [$^{35}$S]-deoxyadenosine and deoxycytosine by multi-primed synthesis (Amersham) to specific activities of $5\times10^9$ cpm/µg. Frozen 10 µm thick sections from the brain basal nuclei of 21 weeks human fetuses were employed for hybridization with these probes as previously described. Exposure under Kodak NTB-2 emulsion was for 5 days at 4° C. Counter-staining was with hematoxilin-eosine. FIG. 6 displays photographs of sections hybridized with AChEcDNA (A,B) and BuChEcDNA (C,D). Pre-treatment with ribonuclease A abolished most labeling (B,D) in both cases. Level of AChEmRNA in multiple brain cells (A) was high as compared with low level of BuChEmRNA transcripts (C). Intensively labeled round large neuronal cells are marked by arrows.

Thus, dot-blot hybridization of fetal brain poly (A)+RNA using $^{32}$[P]-labeled AChEcDNA and BuChEcDNA, indicated low levels (about 0.01% and 0.001% of total mRNA, respectively) for both cholinesterase mRNA transcripts (not shown), in complete agreement with previous oocyte microinjection studies (61). In situ hybridization of these two cDNA probes, labeled with [$^{35}$S], to frozen sections from fetal brain basal nuclei revealed pronounced synthesis of AChEmRNA transcripts in multiple neuronal cell bodies within this brain area, noted for being enriched in cholinoceptive cell bodies (15). In contrast, labeling with BuChEcDNA was considerably lower in basal nuclei sections (FIG. 6), in agreement with previous cytochemical staining studies (62), and pre-treatment with pancreatic RNase abolished labeling with both probes (FIG. 6). Average number of grains per 100µ$^2$ was 160±10 (n=20) and 10±3 (n=20) for the AChE and BuChEcDNA probes, respectively. The ratio between the mRNA transcripts encoding these two enzymes in cholinoceptive brain cells is hence 16:1, close to the 20:1 ratio between their catalytic enzymatic activities (14) and suggesting that the level of active ChEs in human tissues reflects the level of transcription in their corrsponding genes.

Example 7

DNA Blot Hybridization with Labeled ChEcDNA Probes

Figure 7A:
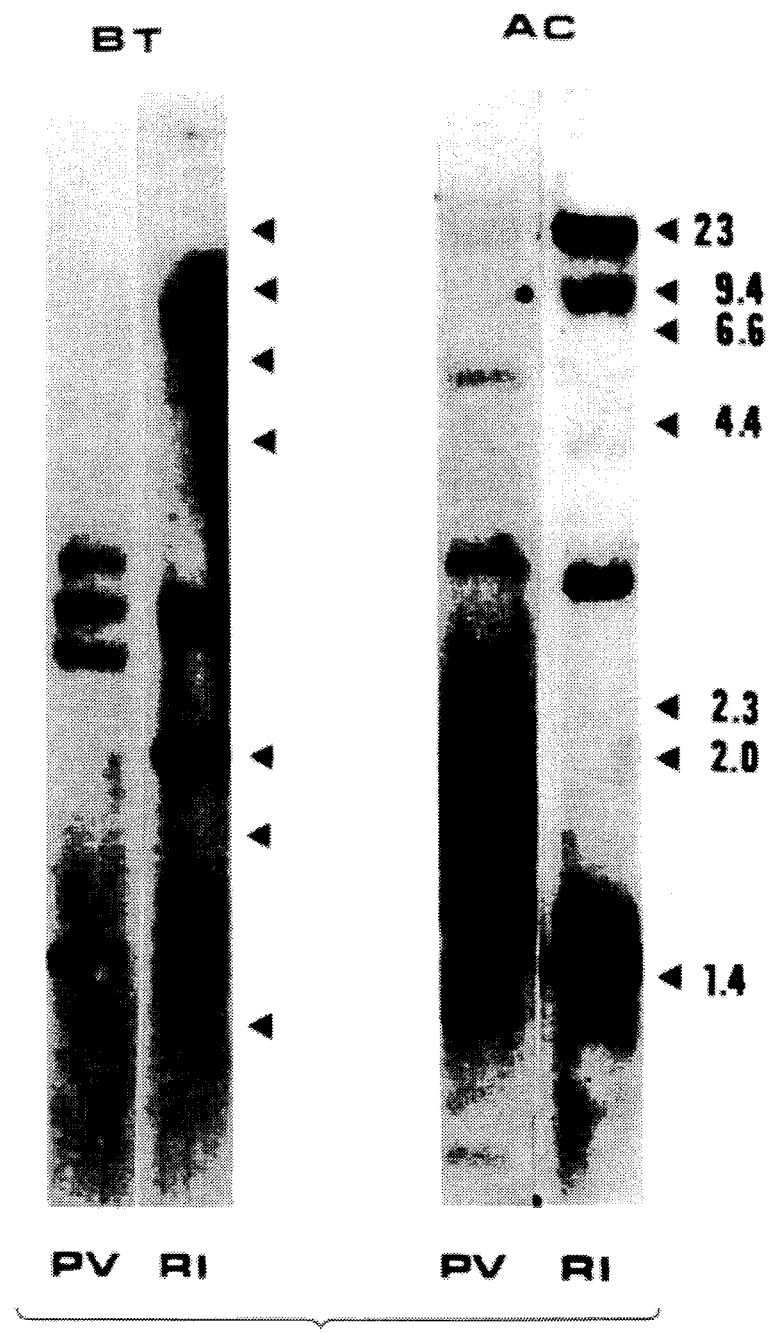
FIG. 7a shows DNA blot hybridization with [$^{32}$P]-labeled AChEcDNA (there is no cross-interaction with BuChEase genes).

Samples of 10 µg of human genomic DNA were enzymatically restricted with EcoRI (RI) or with PvuII (PV) and separated on 0.8% agarose gels. Agarose gel electrophoresis and filter hybridization were as previously described, using AChEcDNA (Ac) or BuChEcDNA (Bt) probes labeled with [$^{32}$P] by multiprime labeling to specific activities of $5\times10^9$ cpm/µg. Exposure was for 10 days with an intensifying screen. Results are shown in FIG. 7a. Lambda phage DNA cut with Hind III served for molecular weight markers (arrows).

The genomic DNA blot hybridized with [$^{32}$P]-labeled probes of AChEcDNA and then BuChEcDNA reveals clear differences between the hybridization patterns obtained with the human genomic DNA sequences encoding BuChE and ACHE, respectively. Although this analysis does not completely exclude the possibility that alteranative splicing from a single gene is responsible to these different patterns, it certainly makes it highly unlikely. New information based on cosmid recombination cloning has now revealed that the gene encoding BuChE does not contain AChE coding sequences (80). Taking into account that there are three sites on human chromosomes that carry DNA sequences encoding BuChE (63,47), this implies the existence of a fourth cholinesterase gene (and perhaps more, although not many, as inferred from the intensity of hybridization) in the human genome. The presence of several EcoRI and PvuII sites in this gene indicates that it includes intervening sequences in addition to the regions represented in the cDNA. Parallel hybridization experiments with genomic DNA from several other species [bovine, rat, chicken and Torpedo (not shown)] revealed a high evolutionary conservation for the AChE genes.

Mapping of the Human Genes Coding for ChEs on Chromosome No. 3

Using in situ chromosomal hybridization, inventors demonstrated that chromosome 3 carries sequences hybridizing with and BuChEcDNA.

In situ hybridization experiments were performed using Q-banded and R-banded chromosome preparations from peripheral blood lymphocytes and the above BuChEcDNA probe labeled with [$^{35}$S].

Chromosome spreads from peripheral blood lymphcytes treated with 5-bromodeoxy Uracil were pre-incubated in 2×SSC (1×SSC=0.15M NaCl and 0.015M sodium citrate), for 30 min. at 70° C. RNA was hydrolyzed by 60 min. incubation at 37° C. in 0.1 mg/ml of pancreatic ribonuclease (Sigma), followed by successive washes of 5 min. in 2×SSC and 70, 80 and 100% ethanol. DNA was denatured by 4 min. incubation at 70° C. in 70% formamide, 2×SSC and 10 mM potassium phaphate buffer at a final pH of 7.0. The chromosome spreads were immediately transferred to frozen ethanol at 100, 80 and 70% concentrations for successive washes of 5 min. and were air-dried. Each spread was then covered by a 25 µl drop of hybridization solution, containing 50% formamide, 10% dextran sulfate, 1×Denhardt's solution (1×Denhardt's solution is 0.02% Ficoll, 0.02% polyvinylpyrrolidone and 0.02% bovine serum albumin) and 8 ng of the preboiled BuChE-cDNA probe, labeled by nick-translation with [$^{35}$S]-adenosine and [$^{35}$S]-cytosine to a specific activity of $1\times10^8$ cpm/µg and purified by three successive precipitations in ethanol, in the presence of 10 W:W Salmon sperm DNA as a carrier. Hybridization was for 18 hrs. at 37° C., in a humid chamber and under cover slides. The chromosomes were washed with 50% formamide and 2×SSC (1HR, 37° C.), 2×SSC (15 min., 37° C.), 2×SSC and 20 mM β-mercaptoethanol (15 min., 37° C.), 2×SSC (15 min., 37° C.), 2×SSC and 20 mM 5-mercaptoethanol (15 min., 37° C.), 2×SSC (15 min., 50° C.) and 0.15×SSC (15 min., 50° C.), dehydrated by successive 5 min. incubations in 70, 80 and 100% ethanol at room temperature and air-dried. Exposure was under photography emulsion (Kodak NTB-2 diluted 1:1 in H$_2$O at 45° C.) in a dry chamber at 4° C. for 12–15 days and development was for 0.5–1.5 min. in D-19 Kodak developer.

Slides were then stained for 15 min. in 150 mg/ml Hoechst 33258 Stain (Aldrich), rinsed in distilled water and dried. To create the R-bands, stained slides were mounted in 2×SSC under coverslips and were illuminated for 30 min. by a mercury vapor lamp at a distance maintaining a temperature of 47°–50° C., rinsed in distilled water and restained in 4% buffered Giemsa (Gurr-R-66) at pH 6.8.

The cumulative distribution of autoradiographic silver grains observed over photographed chromosome spreads were statistically analyzed. The analysis of silver grain distributions from 52 karyotypes indicates BuChE is located in the q21–q26 region of chromosome 3.

Example 8

Detection of Changes of Human ChE Genes Associated with Leukemia and/or Abnormal Megakaryocytopoiesis A. Methods Blood samples were drawn with 5 mM EDTA (pH7.5) from 7 patients (Department of Obstetrics and Gynecology, The Edith Wolfson Medical Center, Holon, Israel) suffering from abnormal platelet counts and leukemias. Blood DNA from 30 apparently healthy individuals served as controls. In addition, DNA from 14 patients with various leukemias was gratefully received from Prof. E. Canaani, The Weizmann Institute of Science. For hybridization experiments, 10 μg samples of purified DNA from peripheral blood were digested to completion with various restriction endonucleases (Boehringer Mannheim), and electrophoretically separated on 1.2% horizontal agarose gels (1.2 mA/cm, 18 hr). DNA was transferred onto GeneScreen membranes (NEN, Du Pont) according to the company's instructions. Filters were subjected to hybridization with electrophoretically purified fragments from AChEcDNA (64) and BChEcDNA (20), 1500 and 2400 nucleotides long, respectively, labeled by "multiprime" DNA polymerase reaction (Boehringer, Mannheim) with [$^{32}$P]-ATP to $5\times10^9$ dpm/μg. The hybridization condition used for detecting human ChE gene sequences was that described in reference 20. Specifically, the blot was incubated at 42° C. for 48 hr with $3\times10^7$ dpm of $^{32}$P labeled DNA probe at a specific activity of $2\times10^9$ dpm/μg, in 50% (vol/vol) formamide/10% dextran sulfate/0.1% bovine serum albumin/0.1% Ficoll/0.1% polyvinylpyrrolidone/50 mM sodium phosphate buffer at pH 6.5/750 mM NaCl/75 mM sodium citrate/75 μg of herring sperm DNA per ml, adjusted with HCl to a final pH of 6.5. The blot was washed in 15 mM NaCl/1.5 mM sodium citrate at 50° C. (four times, 30 mins. each). DNA preparation, hybridization, x-ray film autoradiography and optical densitometry were performed as previously described (66) using the isolated cDNA fragments for quantitative analysis.

B. Amplification of ACHE and CHE Genes (1) Appearance of Amplified ChE Genes in Various Types Leukemia In order to search for putative structural changes within the human ACHE and CHE genes encoding AChE and BuChE, the restriction fragment patterns in peripheral blood DNA from 16 patients with various leukemias as compared with DNA from 30 healthy individuals was first examined. For this purpose DNA blot hybridization was performed with equal amounts of patients' DNA following complete digestion with the restriction endonucleases PvuII and EcoRI and gel electrophoresis (see Methods). Hybridization with [$^{32}$P]-labeled AChEcDNA and BuChEcDNA repeatedly revealed invariant restriction patterns and signal intensities for DNA from all of the healthy individuals. The same restriction patterns and signal intensities were observed in DNA from 12 of the leukemic patients. In contrast, the hybridization patterns in the 4 remaining samples displayed both qualitative alterations and a clear signal enhancement with both cDNA probes. These observations are summarized in Table II hereafter [under (A)].

(2) DNA Blot Hybridization of Leukemic DNA Samples.

Figure 8:
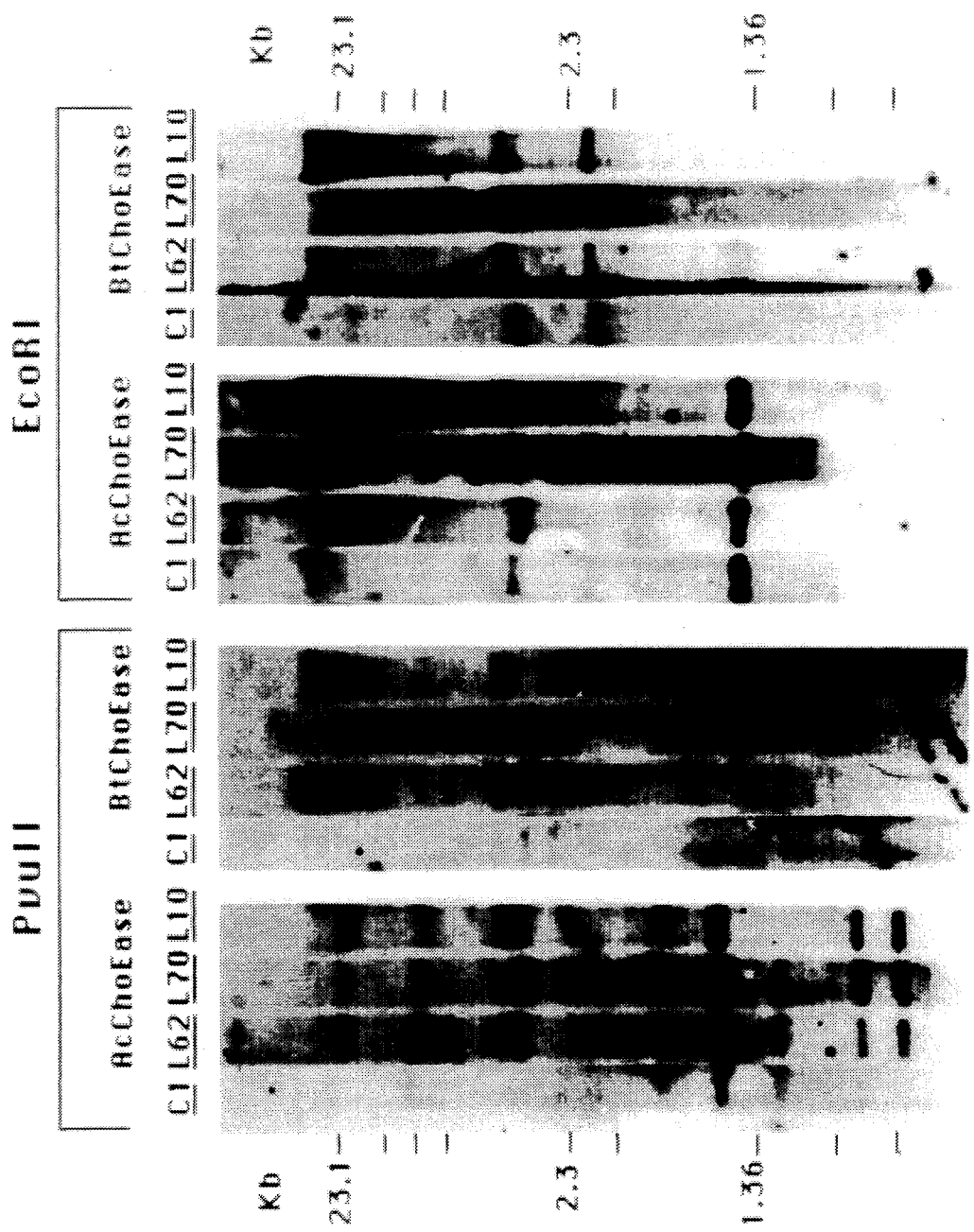
FIG. 8 shows DNA blot hybridization of leukemic DNA samples.

FIG. 8 presents the DNA blot hybridization results obtained with three of the four latter leukemia DNA samples [see under (1)] and with one of the controls. In this experiment 10 μg of peripheral blood DNA from 3 AML cases and one healthy control (L10, L62, L70 and C1, see Table I for details) were subjected to complete enzymatic digestion with the restriction endonucleases PvuII and EcoRI, followed by agarose gel electrophoresis and DNA blot hybridization with [$^{32}$P]-labeled AChEcDNA and BuChEcDNA probes (see Methods). The experimental conditions were as detailed under Methods and in previous publications (5,20, 65,47). Ethidium Bromide staining of the agarose gels was employed to ascertain that equal amounts of DNA were loaded and electrophoretically separated in each of the lanes. Exposure was for 10 days at −70° C. with an intensifying screen. Hind III digested DNA from Lambda and φx174 phages served as molecular weight markers. Results are presented in FIG. 8, revealing intensified labeling signals appeared in bands that are also present in the control bands. Also, in leukemic DNAs novel labeled bands appeared, which are absent from the control lanes.

(3) Appearance of Amplified CHE Genes in Patients with Platelet Disorders

In view of the promising results described under (2) and the previous reports correlating ChE with megakaryocytopoiesis and platelet production (43,44,45,46), DNA from additional patients with platelet disorders, whether or not defined as leukemic was examined. Results are presented in TABLE II hereafter [under (B)]. Significantly enhanced hybridization signals with both cDNA probes were found in 3 out of 5 such patients examined, one of them leukemic. Interestingly, the intensity of hybridization in 2 of these samples was much higher than it was in any of the previously tested leukemic DNA samples.

(4) DNA Blot Hybridization of DNA Samples from patients with Hematopoietic Disorders.

Figure 9:
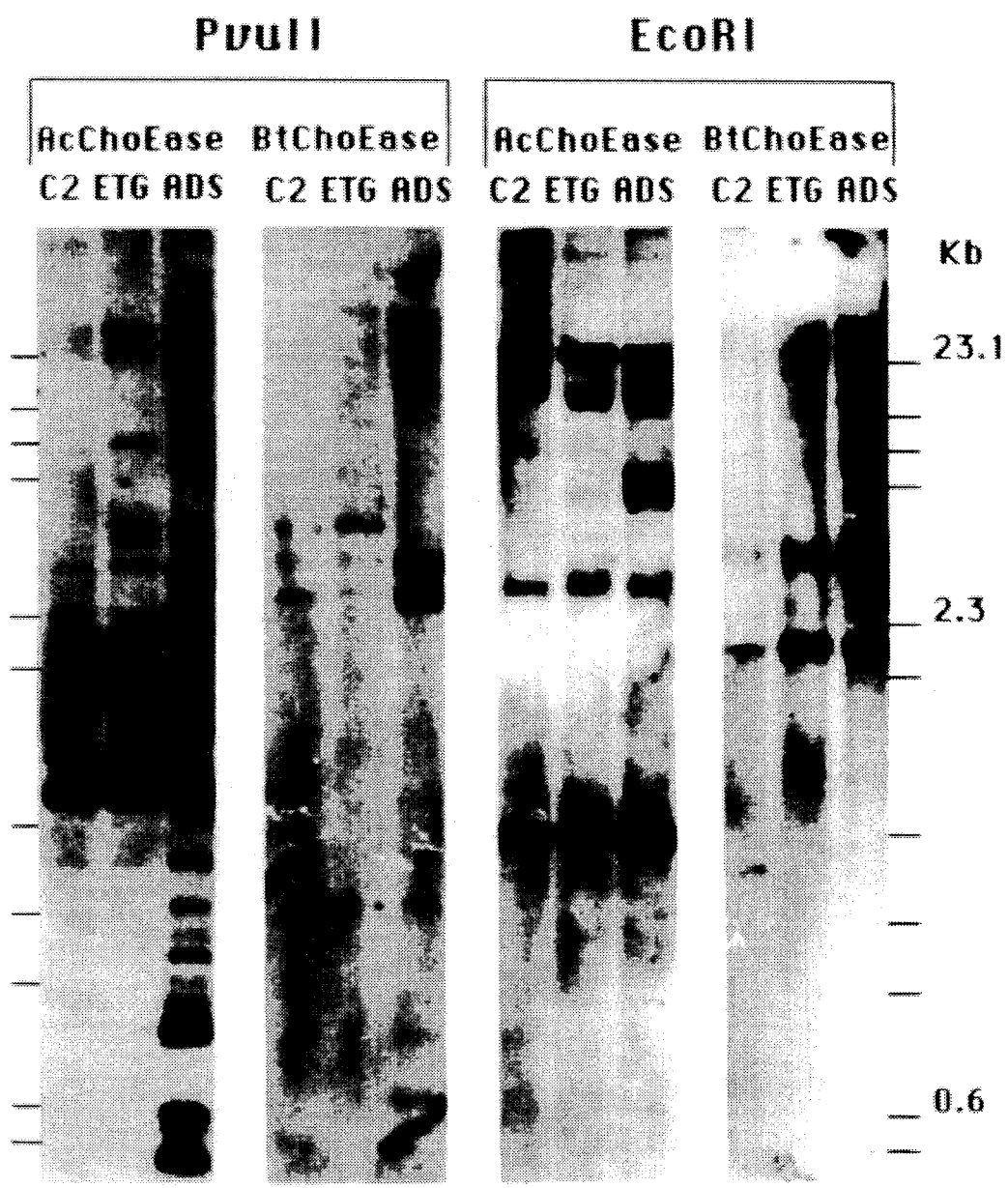
FIG. 9 shows the amplification of AChE and ChE genes in DNA from patients with hematopoietic disorders.

FIG. 9 presents the DNA blot hybridization results obtained from one patient with highly increased platelet counts (ETG), from a leukemic patient with decreased platelet counts (ADS) and from a healthy donor (C2).

Experimental details and conditions were identical with those of the experiment shown in FIG. 8. As may be seen in FIG. 9, there was pronounced enhancement of hybridization signals with both probes. Furthermore, the amplification events in these two samples appeared to involve many additional PvuII-cut DNA fragments, due to either nucleotide changes producing novel PvuII restriction sites, or different regions of DNA having been amplified. This may also be seen in FIG. 10a, described hereafter.

(5) Comparative Analysis of DNA Samples from a Healthy Control, a Leukemic AML Case and a Non-Leukemic Case with Platelet Disorder.

(i) Comparative analysis was performed with representative DNA samples from a healthy control (C1), a leukemic AML case with moderate amplification (ADS) and a non-leuklemic case with pronounced decrease in platelet counts (YED), by DNA blot hybridization using [$^{32}$P]-labeled probes.

Figure 10A:
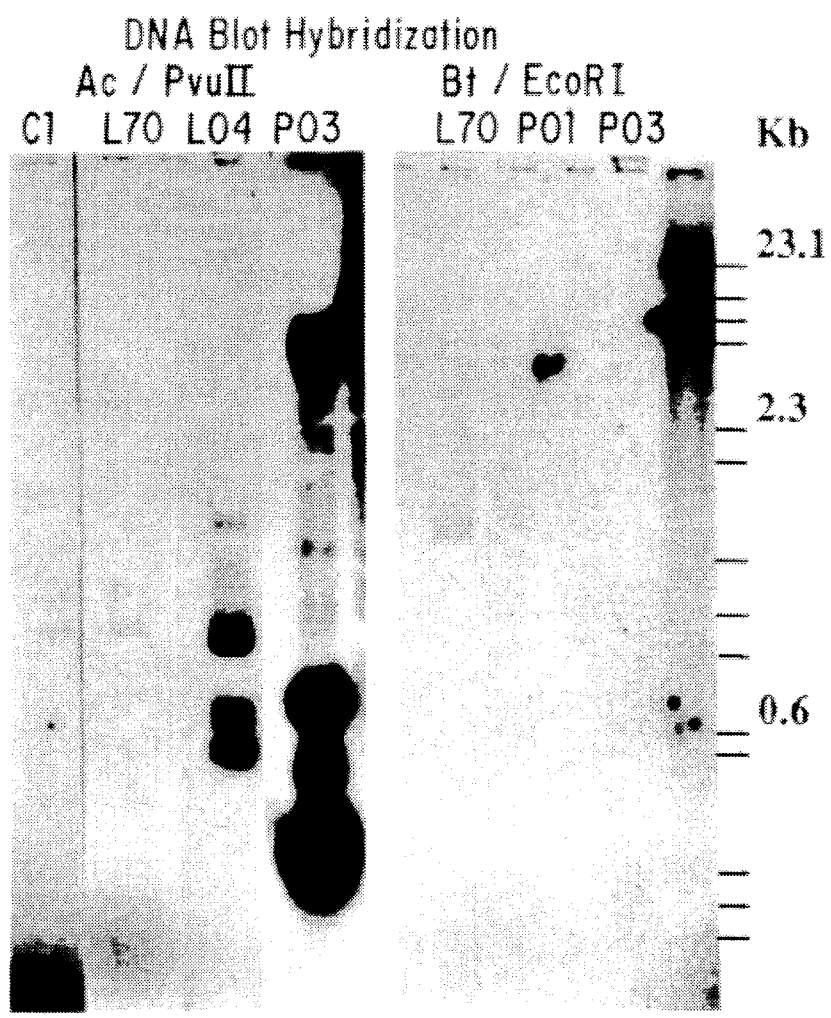
FIG. 10 shows intensified gene amplification, accompanied by structural differences between the amplified DNA regions.

FIG. 10a illustrates blot hybridization patterns with PvuII cut genomic DNA and AChEcDNA probe (Ac) and with EcoRI cut genomic DNA and BuChEcDNA probe (Bt). Conditions were same as those employed in FIG. 8, with exposure for 6 days.

Figure 10B:
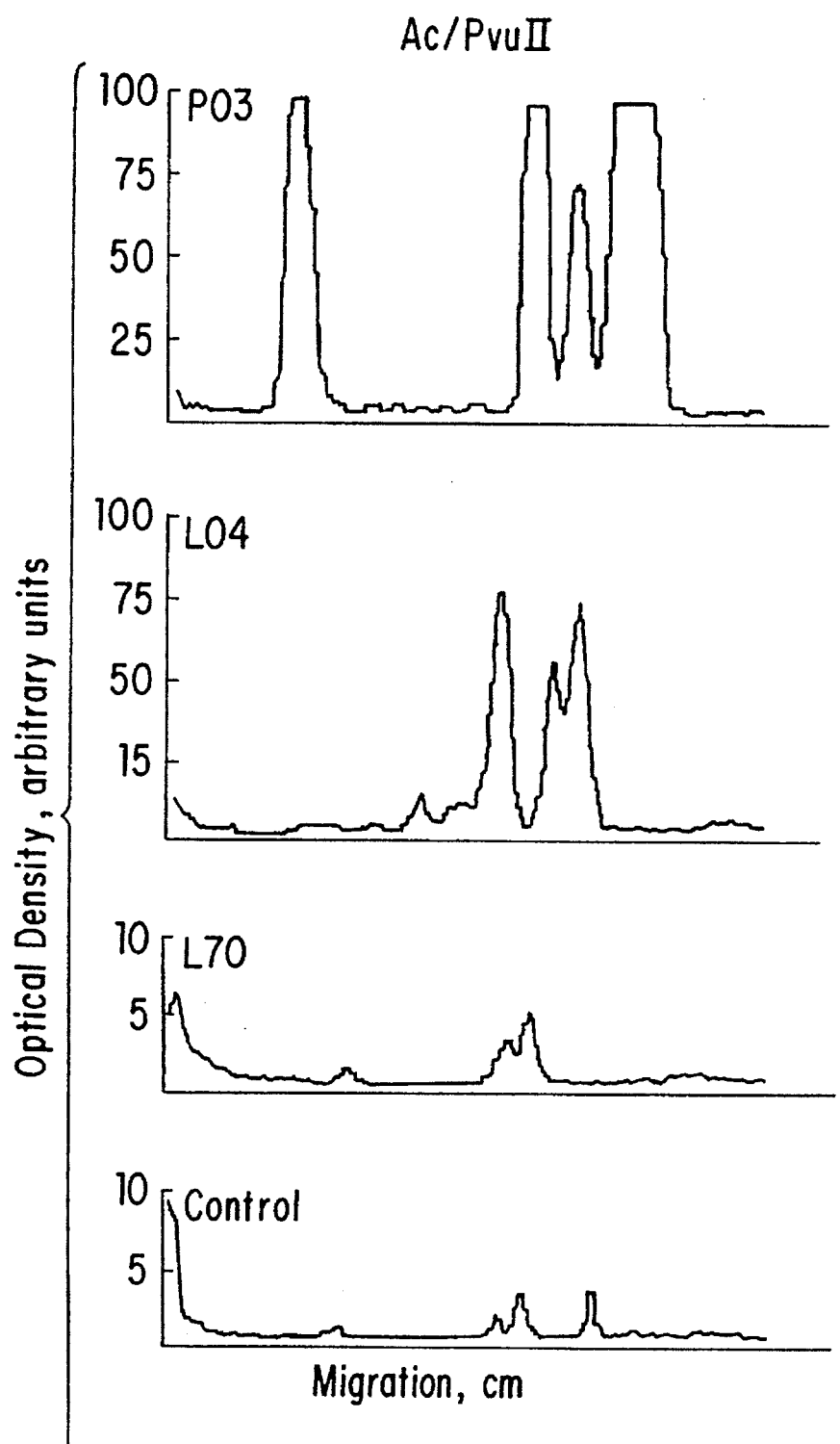

(ii) To further compare the restriction fragment patterns of the amplified genes, the relevant lanes from the above described autoradiograms were subjected to optical densitometry. Results are shown in FIG. 10b. In this experiment, optical densitometry of individual lanes from the PvuII-treated, AChEcDNA-hybridized blot was performed at 545 mμ [details may be found in (72)].

This analysis clearly demonstrates the appearance of slightly enhanced hybridization signals at equal migration positions to those observed in control DNA from a representative leukemic DNA sample, marked L70 (FIG. 10b), with a moderate amplification. In another leukemic DNA sample, marked ADS, and taken from a patient with reduced platelet counts, the densitometry signals were higher by an order of magnitude and presented several additional short PvuII-cut fragments. Yet much higher signals and more novel bands of various sizes were observed with the YED sample, derived from a non-leukemic patient with a pronounced decrease in platelet count (thrombocytopenia). This may also be seen in FIG. 10c, which shows restriction sites for PvuII and EcoRI on the cDNA probes. This Figure shows that the number of PvuII-cut DNA fragments in YED that were labeled with AChEcDNA exceeds their expected number of three fragments based on the PvuII restriction pattern of AChEcDNA, which may either indicate the extension of amplification into intron regions or reflect structural changes and appearance of novel PvuII restriction sites within the amplified DNA sequence.

(6) Quantification of the Amplification Levels in Diseased DNA Samples by Slot-Blot Hybridization The variable degrees of amplification occurring in the genes coding for AChE and BuChE in said individuals were quantified by slot-blot hybridization, using a 5-fold dilution pattern.

Figure 10C:
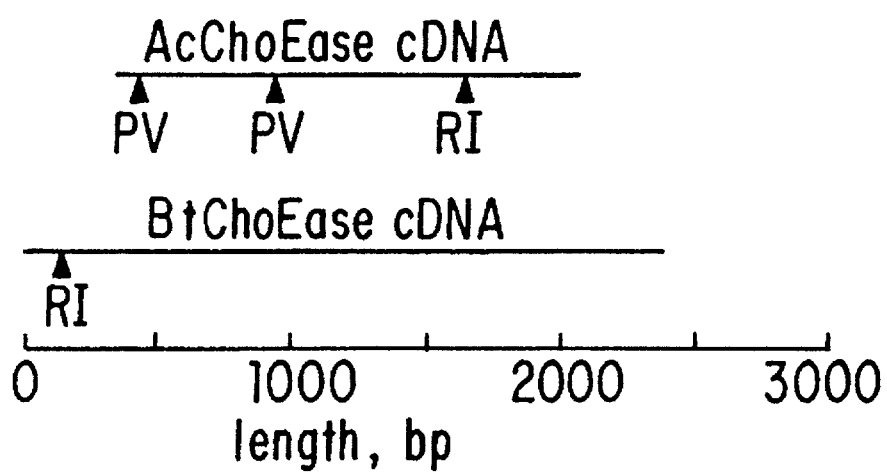
Figure 11:
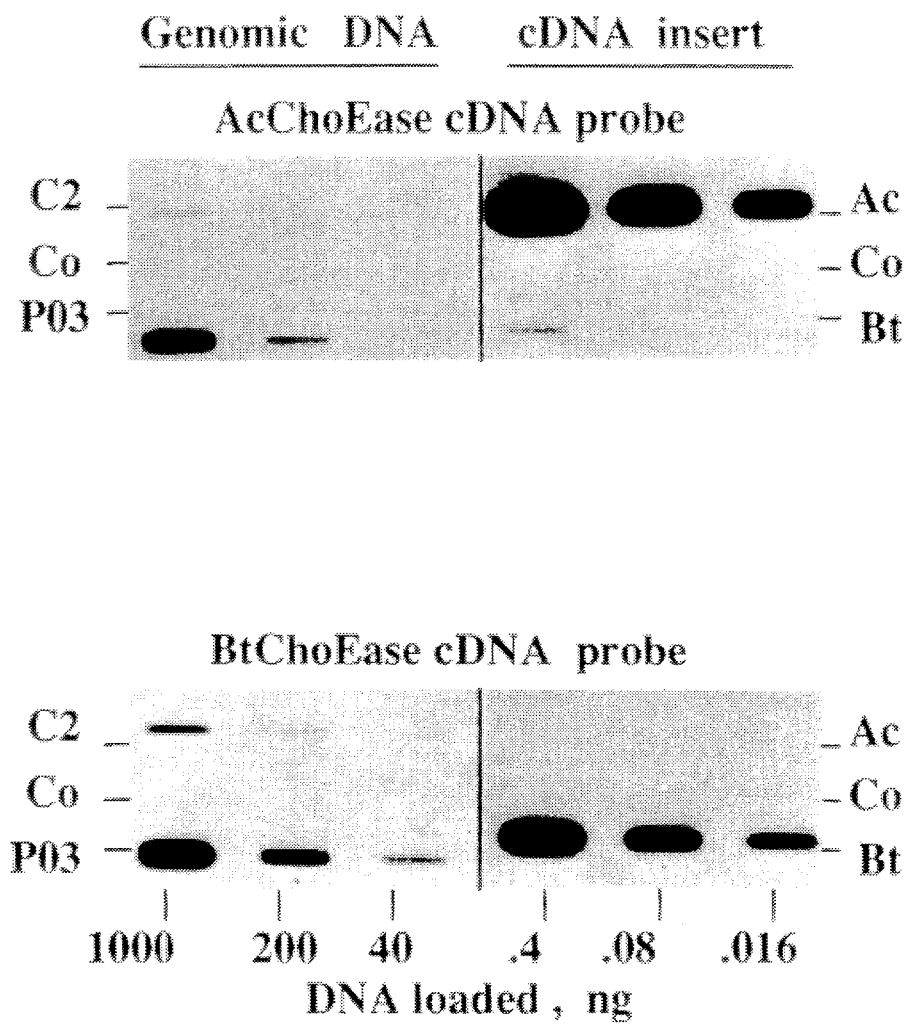
FIG. 11 shows the quantification of the amplification levels in diseased DNA samples by slot-blot hybridization.

In this experiment, denatured genomic DNA from the same 5 individuals that were analyzed in FIGS. 10 was spotted onto a GeneScreen filter using slot-blot applicator (Bio-Rad). Electroeluted AChEcDNA (Ac) and BuChEcDNA (Bt) inserts (FIG. 10c) were spotted in parallel for calibration. Herring testes DNA (Co) served as a negative control. All samples contained the noted quantities of genomic or insert DNAs supplemented with denatured Herring testes DNA to yield a total of 2 µg-DNA per slot. Hybridization, wash and exposure were done with [$^{32}$P]-labeled AChEcDNA or BuChEcDNA [for details see (66]. Results are shown in FIG. 11.

Cross hybridization between AChE and BuChE cDNA probes was exceedingly low (less than 0.01), demonstrating that the observed amplification events indeed occurred in each of these genes and did not merely reflect similarity in their sequences. As may be seen in FIG. 11, 1 µg of YED DNA included genomic sequences equivalent to at least 1 ng of each purified DNA sequence. Taking the total complexity of human genomic DNA as $4\times10^9$ bp, this implies that more than 1000 copies of these sequences are present in YED's DNA. ADS' and ETG's DNAs featured about 20- and 40-fold lower signals, respectively, with BuChEcDNA and, in the case of ADS, somewhat weaker signals with the AChEcDNA, reflecting more modest amplifications in an order of up to 100 copies per genome, in itself a remarkable level.

A summary of the appearance of amplified CHE genes in patients with hematocytopoietic disorders is given in TABLE II.
Footnotes to TABLE II:
1. Peripheral blood DNA from 14 leukemic patients was received, together with clinical classification of the disease type, from Dr.E. Canaani, The Weizmann Institute of Science. Two other patients (LO3 and ADS) were diagnosed and classified in the Department of Obstetrics and Gynecology, The Edith Wolfson Medical Center, Holon, Israel. (AMegL: Acute megakaryocytic leukemia; AMoL: Acute monocytic leukemia; AMML: Acute monocytic/myeloid leukemia; AMLM2: FAB sub-classification of AML).
2. The characteristic types of hematopoietic progenitor cells which appear to be defective in each class of the screened leukemias are noted (50).
3. The approximate extent of amplification was separately determined for the ACHE and CHE genes by slot-blot DNA hybridization and optical densitometry. Numbers reflect the fold increase in number of copies as compared with control DNA. N=normal.
4. Peripheral blood DNA from 5 patients from said Department of Obstetrics and Gynecology, suffering from abnormal platelet counts, was analyzed as detailed above. Abnormalities in platelet counts are noted, where "low" implies<80,000/mm$^3$ and "high"→500,000/mm$^3$ (normal counts are considered 150,000–400,000 platelets/mm$^3$). Note that ADS (No. 16) appears twice.
5. DNA samples from apparently healthy individuals with normal platelet counts of blood ChE activities served as controls and were analyzed as detailed above. C1 and C2 correspond to representative control DNAs, shown in FIGS. 8–11. Similar results ware obtained in 28 more controls (not shown).

TABLE II

A. Leukemias[1]

| No. | type | defective progenitors[2] | Approx. Amplification[3] | |
|---|---|---|---|---|
| | | | AcChoEase | BChoEase |
| 1 L23 | AML | myeloid | N | N |
| 2 L38 | AMegL | promegakaryocytes | N | N |
| 3 L26 | AMOL | monocytes | N | N |
| 4 L10 | AML | myeloid | 30–60 | 30–60 |
| 5 L41 | AMML | myeloid/monocytes | N | N |
| 6 L42 | AML | myeloid | N | N |
| 7 L79 | AML | " | N | N |
| 8 L70 | AML | " | 25–50 | 25–50 |
| 9 L20 | AML | " | N | N |
| 10 L96 | AML | " | N | N |
| 11 L62 | AMML | myeloid/monocytes | 25–50 | 25–50 |
| 12 L59 | AMML | " | N | N |
| 13 L15 | AML | myeloid | N | N |
| 14 L12 | AML | " | N | N |
| 15 L03 | AMLM$_2$ | " | N | N |
| 16 ADS | AMLM$_2$ | " | 50–100 | 30–60 |

B. Megakaryocytopoietic disorders[4]

| No | platelet count | defective progenitors[2] | Approx. Amplification[3] | |
|---|---|---|---|---|
| | | | AcChoEase | BChoEase |
| 16 ADS | low | promegakaryocytes | 50–100 | 30–60 |
| 17 ETG | high | " | 20–40 | 20–40 |
| 18 RLI | low | " | N | N |
| 19 YED | " | " | 500–1000 | 350–750 |
| 20 TLK | " | " | N | N |

C. Controls[5]

| No | platelet count | defective progenitors[2] | Approx. Amplification[3] | |
|---|---|---|---|---|
| | | | AcChoEase | BChoEase |
| 21 C1 | normal | none | N | N |
| 22 C2 | " | " | N | N |

SUMMARY

Altogether, 6 cases of co-amplification within the ACHE and CHE genes were observed in DNA samples from 20 patients with abnormal hematocytopoiesis, while DNA from 30 healthy individuals showed no amplification or polymorphism with respect to the restriction patterns obtained with these probes. The DNA samples presenting these amplifications were derived from 4 cases of AML with 20–100 copies of both ACHE and CHE genes, and 3 cases of platelet count abnormalities, one with excess platelets count, and 20–40 copies of ACHE and CHE genes, and two others with reduction of platelets count featuring up to 1000 copies of the same genes. These striking concomitant multiplications, summarized in TABLE II, present a highly significant correlation ($p<0.01$) between amplifications of ChE-encoding genes and the occurrence of abnormal myeloid progenitor cells or promegakaryocytes in the examined individuals.

It has thus been shown that the cDNA of the present invention may be used for preparation of probes which may be used to diagnose abnormalities in the human ACHE and CHE genes, associated with various hematopoietic disorders. It has been shown herein that said cDNA probes detected the presence of multiple copies of the genes coding of ChEs in a considerable fraction of the leukemic DNA samples examined.

Apart from their diagnostic value, the therapeutic potential of the genetic sequences and proteins of the invention, in treatment of blood cells disorders is also contemplated. Of particular importance is the non-balanced amplification of the AChE gene, which may predict abnormal expression patterns.

Example 9

Detection of Changes in AChE and ChE Genes in Primary Ovarian Carcinomas

Materials and Methods

Primary tumor samples. Specimens of primary tumors were obtained at surgery, frozen immediately in liquid nitrogen and stored at −70° C. until used. Tumor subclassification was performed by standard pathological techniques. DNA and poly (A)+RNA were prepared as previously detailed (47 and 61, respectively).

cDNA and plasmid probes. AChEcDNA and ChEcDNA were prepared as previously reported (73). The C-RAFI plasmid was from Amersham. V-SIS, C-FES and C-MYC (third exon) DNA probes were gratefully received from Opher Gileadi (Jerusalem).

Blot and in situ hybridization. [$^{32}$P]- and [$^{35}$S]-labeled cDNA plasmid probes were prepared by the multi-prime labeling method (Boehringer Mannheim) using enzymatically restricted and gel electroeluted DNA fragments (see (20) and (69) for details). DNA and RNA blot hybridizations were performed as previously described (20,73). In situ hybridization was done with consecutive 10 µm thick Cryostat sections from the above tumor samples as detailed (71). Immunocytochemical staining cytochemical staining of cholinesterase were performed as described (70).

Xenopus oocytes microinjection. Oocytes were injected, homogenized and assayed as detailed (61,77) with 50 ng of poly(A)+RNA from primary ovarian carcinomas or with Barth medium for controls. Oocyte incubation was 18 hrs at 19° C. and further enzymatic assays were performed for 48 hrs at 21° C. Data represent average values of 3 determinations with up to 20% deviation.

Enzymatic activity measurements. Cholinesterase activities were measured spectrometrically by monitoring the hydrolysis of acetyl- or butyrylthiocholine in the presence of 5,5'-dithionitrobenzoic acid as previously described (70,71) or radioactively by measuring the release of [$^3$H]-acetate from acetylcholine (61). 5–10 µl samples of 1:10 (w:v) tissue or oocyte homogenates in PBS (the equivalent of approximately 1 µg tissue or one half oocyte) were assayed at room temperature. Rates of spontaneous substrate hydrolysis were calculated, averaged and subtracted in both cases. Either 10–5M 1,5-bis (allyldimethylammoniumphenyl)-pentan-3-one dibromide (BW284C51, AChE-specific) or 10–5M tetra isopropylpyrophosphoramide (iso-OMPA, ChE-specific) were used for selective inhibition experiments. iso-OMPA was pre-incubated with the samples 40 min prior to the addition of substrate to ensure complete irreversible binding.

(1) Co-amplification of the AChE and ChE genes in primary ovarian carcinomas.

10 µg samples of DNA from 3 primary ovarian carcinomas (Nos. 1,5 and 8, TABLE III), 1 benign ovary (No. 19, TABLE III) from a patient with a unilateral ovarian tumor and 1 brain DNA sample from an apparently normal individual (B) were subjected to complete enzymatic digestion with the enzymes EcoRI or RsaI, followed by agarose gel electrophoresis and DNA blot hybridization with 1.5 Kb long [$^{32}$P]-AChEcDNA probe (64) or with a 2.4 Kb long [$^{32}$P]-ChEcDNA probe (20). Experimental details were according to previous publications ((69) and (73)). Ethidiumbromide staining of the agarose gels was employed to ascertain that equal amounts of DNA were loaded and electrophoretically separated in each of the lanes. Exposure was for 10 days at −70° C. with an intensifying screen. Hind III digested DNA from lambda phage and Hae III digested DNA from Φ×174 phage served as molecular weight markers. Internal RsaI restriction sites were found in both of these probes, whereas an EcoRI site exists in ChEcDNA but not in the AChEcDNA probe employed. Intense hybridization signals, reflecting gene amplification, with both these probes, which were shown to be non-cross reactive with each other (73), may be seen in FIG. 1. It should also be noted that the probes used apper to co-label the same genomic DNA fragments in all tumors analyzed.

Figure 12:
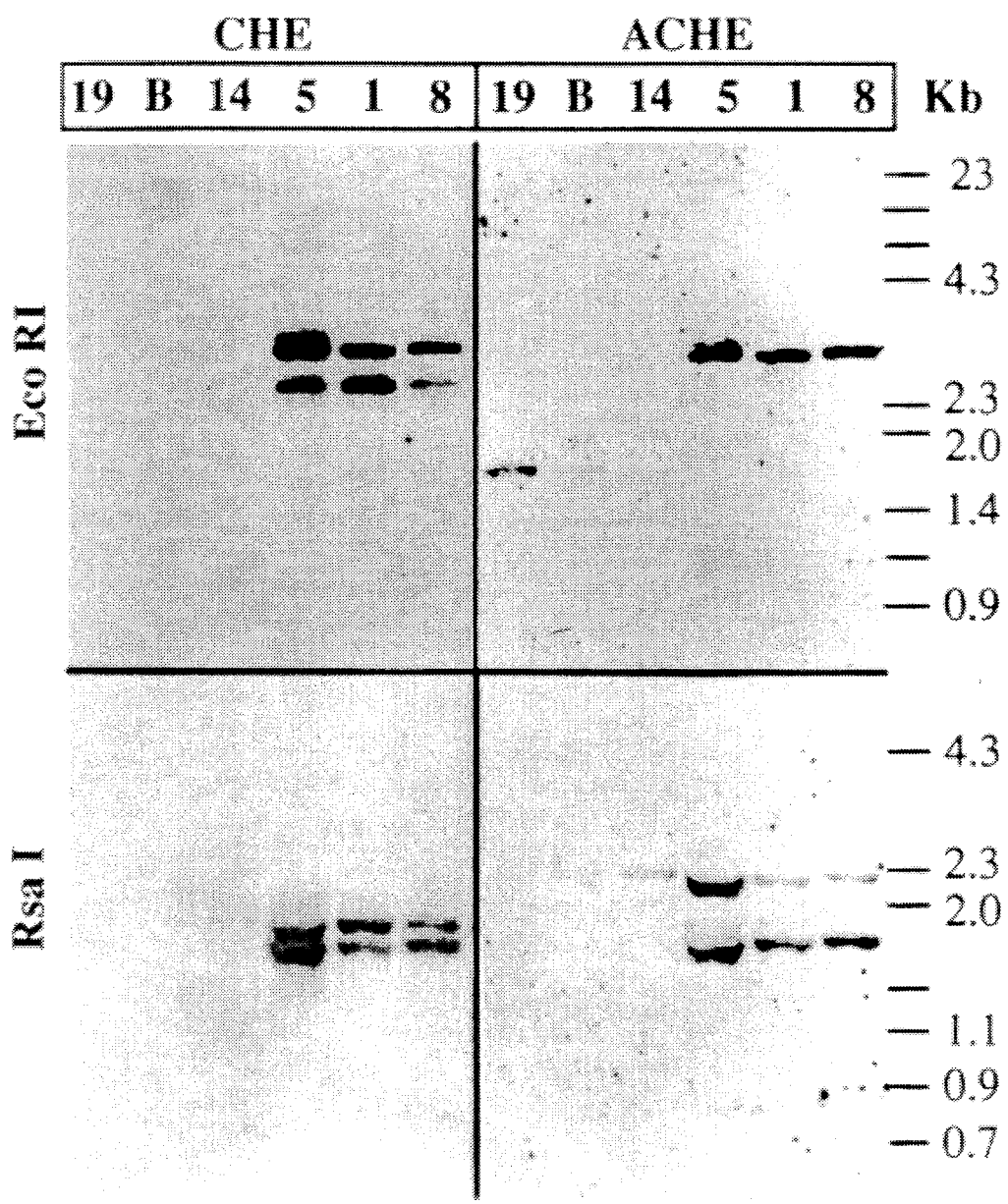
FIG. 12 shows the co-amplification of the AChE and ChE genes in primary ovarian carcinomas.

It may be seen from this Example that when DNA from untreated ovarian carcinomas was subjected to enzymatic restriction and blot hybridization with [$^{32}$P]-ChEcDNA, amplified hybridization signals were clearly observed with both probes in 6 out of 11 malignant tumors, but not in benign ovarian tissues (FIG. 12). In each case of amplification, novel bands were observed in addition to those representing the normal AChE and ChE genes. Moreover, the two non-homologous cDNA probes, which were previously shown not to cross-hybridize (73) appeared to co-label novel restriction fragments of similar sizes, cut with both EcoRI and RsaI, in DNA samples having the co-amplification and under exposure conditions where the normal genes were hardly detectable. In contrast, no such co-labeled fragments were found in DNA samples with normal AChE and ChE genes (FIG. 12).

(2) Structural alterations in the amplified ChE genes in ovarian carcinomas (A) Ten microgram samples of DNA from 5 ovarian carcinomas (Nos. 1, 4, 5, 8 and 9, TABLE III) and 1 peripheral blood sample from a healthy individual (see No. 20, TABLE III and (69) for details) were subjected to complete enzymatic digestion with the enzymes Hind III, EcoRI and TaqI, followed by agarose gel electrophoresis and DNA blot hybridization with [$^{32}$P]-ChEcDNA (20). Experimental conditions were similar to those of FIG. 12. The low intensity signal obtained with the normal ChE gene (No. 20) and the reproducibly altered structure of the amplified ChEDNA fragments should be noted.

(B) Restriction site mapping of ChEcDNA (20), which reflects that of the amplified genes in ovarian tumors (FIG. 13A) was performed with enzymes EcoRI (E), TaqI (T) and RsaI (R). Results suggest similar structural properties. Initiation (AUG) and Termination (UAA) sites are noted. The position of the three introns (i1–3) in the human ChE gene was determined by analysis of genomic clones (73, 74). (A)n=3'-poly(A) tail. The coding sequence is represented by shaded areas.

(C) To ascertain the specificity of hybridization, used DNA blots were re-hybridized with a plasmid DNA probe from C-RAFI protoncogene (Amersham), wich also detected amplified DNA sequences in these primary tumors (TABLE 3). This probe labeled a single, different band in all of the tumors, confirming that hybridization signals with the AChEcDNA and ChEcDNA probe indeed reflected the true amplification of genuine genomic sequences and were not due to plasmid DNA contaminations (not shown).

Figure 13A:
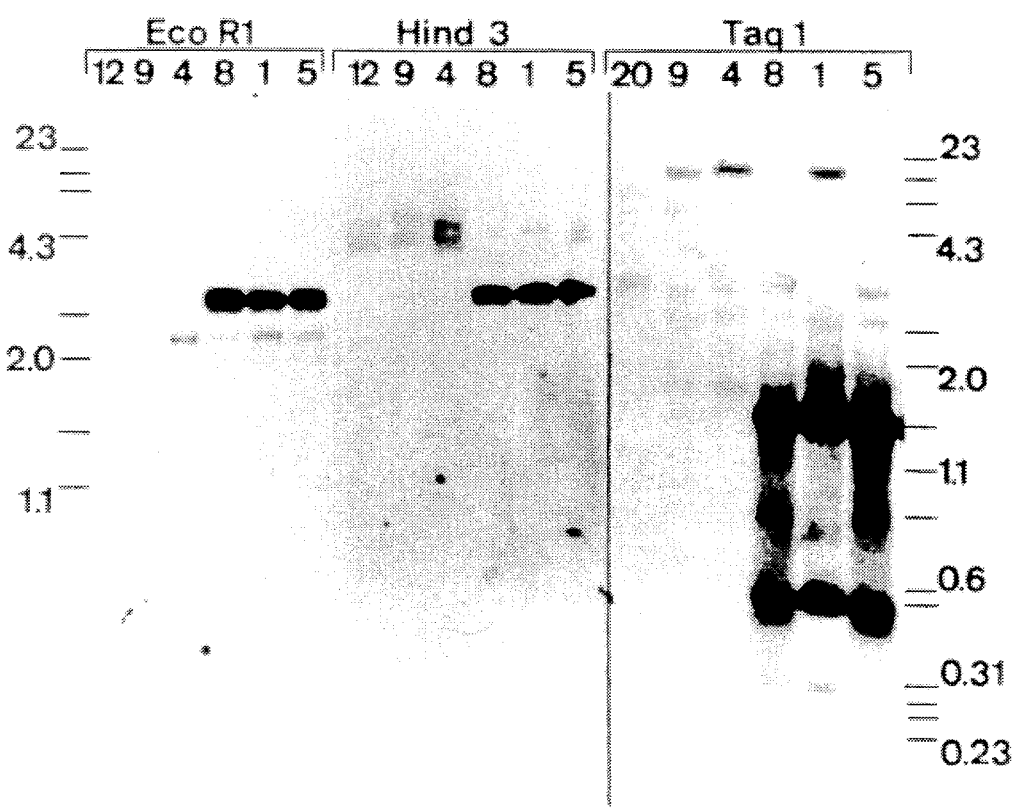
FIG. 13 shows DNA blot hybridization of ovarian carcinomas samples with BuChEcDNA.
Figure 13B:
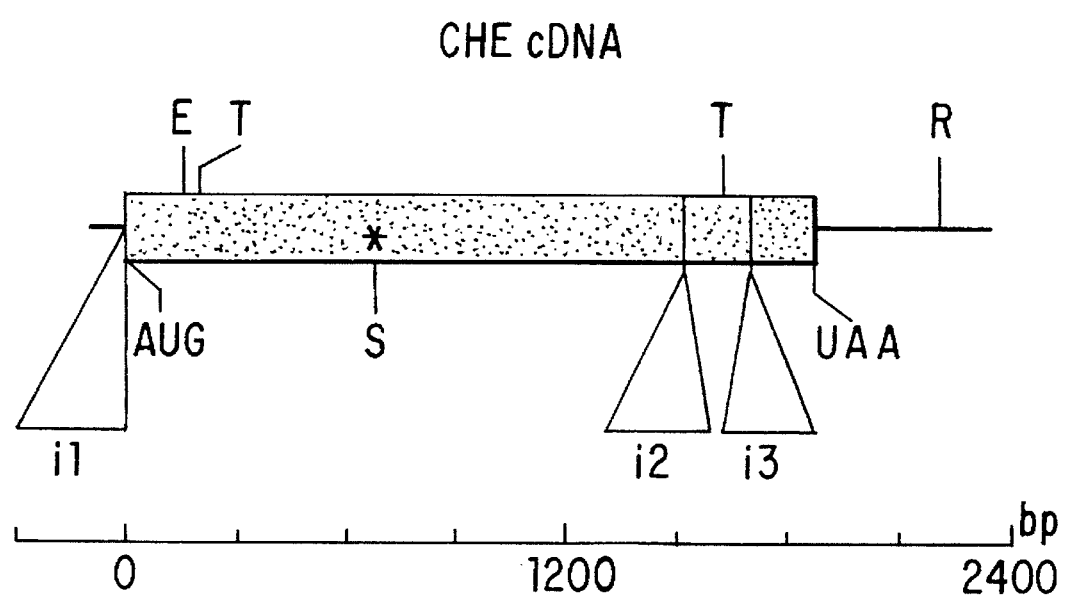

It is of interest that the amplified ChEcDNA sequences appeared not to include the internal Hind III restriction site characteristic of the normal, intron-containing ChE gene (FIG. 13, (74)(75)). Furthermore, TaqI generated the major fragments of 1400 and 1600 base pairs from amplified ChE genes in each of these tumors, which could hace indicated that the core amplification unit was composed of processed, intron-less ChEcDNA that includes such TaqI sites (20,21) (FIGS. 13A and 13B). However, PCR amplification data have shown that introns were present in the amplified gene.

(3) Co-amplification of the AChE and ChE genes with C-RAFI and V-SIS oncogenes demonstrated by dot-blot hybridization.

Quantification of the AChE and ChE genes co-amplification in DNA samples from malignant and benign tumor issues (TABLE III) was performed by dot-blot DNA hybridizations followed by optical densitometry of blot autoradiograms in comparison with the purified ChEcDNA and AChEcDNA inserts (for details see (69),(72)). Parallel blots were hybridized with DNA probes for the oncogenes C-RAFI (Amersham) and V-SIS (gratefully received from Opher Gileadi). Blots presented include series of 2-fold dilutions of μg quantities of genomic DNA preparations. The amplified signals in several of the examined samples and the co-amplification of the C-RAFI and V-SIS oncogenes in part, although not all of these samples should be noted. Representative calibration blots with pg quantities of the relevant purified cDNA inserts are included (center). Examples for the blot hybridization analyses and a summary of the data are presented in FIG. 14 and TABLE III.

Figure 14:
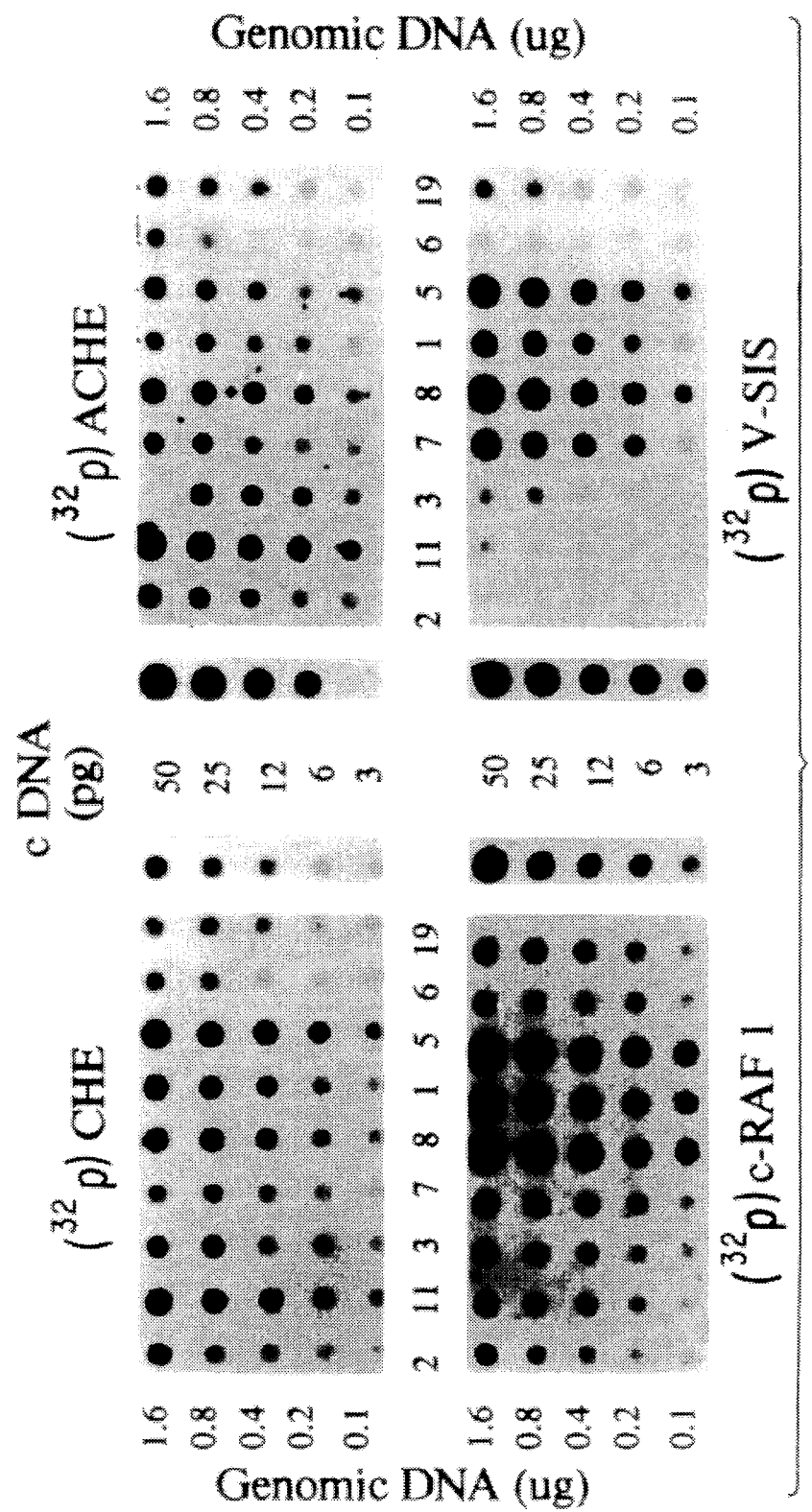
FIG. 14 shows the co-amplification of the AChE and ChE genes with C-RAFI and V-SIS oncogenes, demonstrated by dot-blot hybridization.

The aforementioned DNA samples from 6 malignant ovarian tumors included 7–23 pg of AChEcDNA and 20–60 pg of ChEDNA per μg genomic DNA whereas DNA samples from four healthy control tissues and five benign tumors that were thus examined were found to include AChEDNA and ChEDNA sequences equivalent to 1–7 pg of AChEcDNA and ChEcDNA per μg (FIG. 14, TABLE I). These data reflect up to 10- or more fold amplilfcation of the AChE and the ChE genes in those ovarian tumors. Hybridization with regional ChEcDNA probes (69) indicated that the amplified DNA included the entire ChE coding sequences (not shown). Parallel hybridizations with cDNA probes from four different oncogenes revealed pronounced amplifications of the protein kinase oncogenes C-RAFI and C-FES as well as the growth-factor oncogene V-SIS in three of the six tumors having AChE and/or ChE gene amplifications. Interestingly, these were the tumors with higher levels of amplified AChEDNA and ChEDNA sequences and higher ratios between ChE:AChE gene amplifications. No amplification in the third exon from C-MYC, a nuclear protein oncogene, was observed in any of these primary tumors. There was no apparent correlation between any of these gene amplifications and patient age.

(4) Expression of full-length ChEmRNA and existence of translatable ChEmRNA in ovarian carcinomas.

(A) Ten microgram sample of poly(A)+RNA from a representative ovarian carcinoma tumor (Oc, No. 8 in TABLE 1 and FIGS. 12 and 13) and from fetal human adrenal (Ad), kidney (Ki), liver (Li) and heart (He) (17 weeks gestation) were subjected to gel electrophoresis and RNA blot hybridization with [$^{32}$P]-ChEcDNA (for details see Prody et al., 1987). Repeated hybridization of the same blot with another cDNA probe, termed TH 14, revealed low intensity signal in all lanes (not shown), implying that the intensified labeling of 2.4 Kb ChEmRNA in the tumor tissue was specific and was not due to RNA overloading. Ribosomal RNA (28S, 5 Kb and 18S, 2 Kb) served for size markers. Exposure was for 5 days at –70° C. with an intensifying screen. RNA blot hybridization of poly(A)+ RNA from normal ovary revealed no signal at all (79).

(B) Fifty nanogram samples of poly(A)+RNA from the same primary tumor referred to under A were injected into *Xenopus laevis* oocytes and the resultant acetylcholine (ACh) hydrolyzing activities (+) were measured (for details see (61),(77)). Barth-medium injected oocytes served as controls (–). The selective inhibitors 1,5-bis (4-allyl-dimethyl-ammoniumphenyl)-pentan-3-one (BW284C51) and tetraisopropylpyrophosphoramide (iso-OMPA) were both employed in final concentrations of 1.10–5M to specifically block the activities of AChE and ChE, respectively. The intensive production of ChE activity in the tumor mRNA-injected oocytes should be noted (for comparison, fetal brain mRNA induces 1.4 nmol ACh hydrolyzed per μg RNA).

As may be seen from this Example (Table III), measurements of AChE and ChE catalytic activities in soluble and membrane associated fractions from tumor homogenates revealed variable levels of both enzymes, in the range of 100–1000 nmol acetylthiocholine and butyrylthiocholine hydrolyzed per min. per gram tissue. There was no correlation between the level of soluble or membrane-associated enzyme activities and the extent of AChEDNA and/or ChEDNA amplifications (TABLE III). However, the ChE activities in tumor homogenates could be accounted for by residual blood contaminations, capable of contributing ChE activities in the range of several μmol/min/ml (76). Similarly, residual erythrocyte contaminations could explain the measured AChE activities. Therefore, the question of whether the amplified AChEDNA and ChEDNA sequences were expressed as active hydrolytic enzymes could not be resolved by enzyme activity measurements.

Figure 15A:
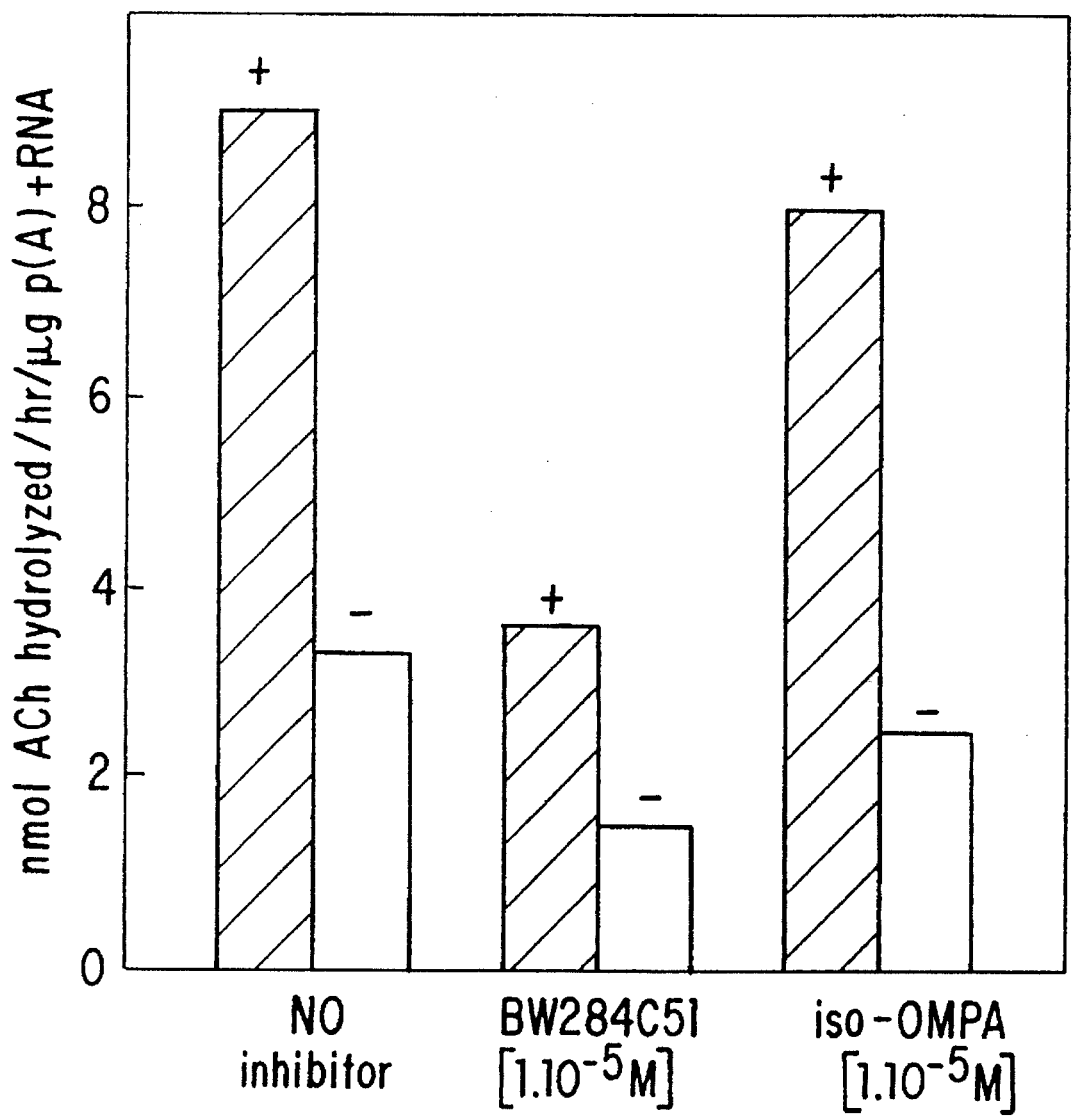
FIGS. 15a, FIG. 15b shows the expression of full length ChEmRNA (by RNA hybridization) and the translatable ChEmRNA in ovarian carcinomas (by *Xenopus* oocyte microinjection).
Figure 15B:
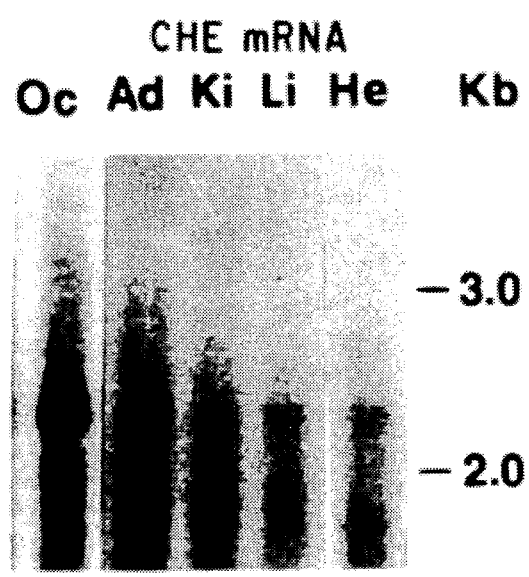
Figure 16A:
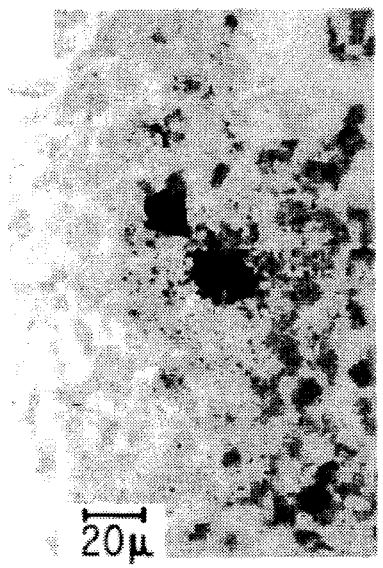
FIG. 16 shows the focal expression of the amplified AChE and ChE genes as demonstrated by in situ hybridization and immunochemical and cytochemical staining.
Figure 16B:
Figure 16C:
Figure 16D:

The presence of ChEmRNA transcripts in the ovarian tumors was first persued by RNA blot hybridization. This analysis revealed, in three of the tumors bearing amplified ChEDNA, significantly enhanced labeling of a full-length 2.4 KB ChEmRNA relative to that observed in normal ovarian tissue (5) and in other normal developing tissues (FIG. 15A). The G,C-rich AChEcDNA probe tends to bind non-specifically to multiple RNA bands and gave inconclusive results. However, when poly(A)+RNA from such ovarian tumors was microinjected into *Xenopus* oocytes, it directed the synthesis of both AChE and ChE activities, sensitive to the selective inhibitors BW284C51 and iso-OMPA, respectively. The levels of induced activities were about twice as high as those measured for brain AChEmRNA ((61)(77, FIG. 15B).

(5) Focal expression of the amplified AChE and ChE genes as demonstrated by in situ hybridization and immunochemical and cytochemical staining.

As may be seen in FIG. 16, consecutive 10 μm thick cryostat sections from a representative ovarian tumor(No. 3, see TABLE 3 and FIG. 12 and 13) were subjected to in situ hybridization with [$^{35}$S]-ChEcDNA (A) or [$^{35}$S]-AChEcDNA (B), cytochemical staining with acetylthiocholine complexes (C) or fluorescence labeling with monoclonal antibodies to AChE (D), all performed as previously detailed (77,78,70, respectively). Haematoxin-eosin served for counterstain. The sections presented were 100 µm apart. The following should be noted: (a) the central position of the four types of labeling within the tumor tissue; (b) the focal nature of the labeled cells and (c) the presence of small rapidly dividing cells at the center of the labeled area.

Thus, the expression of the mRNA transcripts produced from the amplified AChE and ChE genes was further assessed in frozen tissue sections, where the presence of mRNA transcripts could be demonstrated by in situ hybridization, their protein product by immunocytochemical staining with monoclonal anti-AChE antibodies (78), which cross-react with ChE (70), and enzymatic activity by cytochemical staining with acetylthiocholine compexes (70). When consecutive sections from single tumors were subjected to these three analyses, tumor foci were revealed in which the AChE and ChE genes were highly expressed, with clear colocalized labeling by the three techniques (FIG. 16). These loci were limited to malignant tumors bearing the amplified AChE and ChE genes, and were not observed in any of the other tissue types that were examined. Labeled areas were localized deep within the tumor tissue and contained primarily small, rapidly dividing cells. Semi-quantitative analysis of the in situ hybridization results demonstrated that only 8–12% of the examined areas were significantly labeled with the ChEcDNA probe ($100\pm15$ grains/$100\mu^2$ as compared with $6\pm3$ grains/$100\mu^2$ in unlabeled areas (n=25 fields)). Parallel analysis with the AChEcDNA probe on sequential sections from the same tumors revealed that 9–14% of the analyzed cells were significantly labeled ($85\pm14$ grains/$100\mu^2$ over $7\pm2$ grains/$100\mu^2$ in unlabeled areas (n=25 fields)). Labeling was sensitive to RNase treatment reproducibly focal in nature.

FOOTNOTES TO TABLE III a. DNA was extracted from (A) 11 primary ovarian carcinoma tumors clinically classified as noted, prior to any treatment (ad.ca: adenocarcinoma); (B) from 5 benign ovarian tumors and (C) from 4 other tissue sources, as noted. (See (68) for detailed classification of ovarian carcinomas).

b. ACHE and CHE activities, in nmol of acetylthiocholine and butyrylthiocholine hydrolized per min per g of tissue, were determined radiometrically or spectrophotometrically as detailed elsewhere (61,77). Subcellular fractionation to soluble and membrane-associated fractions was performed as described (70). Spectrophotometric assays were performed in multiwell plates 5–6 time points were measured in a Bio-Tek EL-309 microplate reader. Radioactivity measurements were performed in triplicates. Spontaneous hydrolysis of substrate was subtracted in both cases, and rates of enzymatic activity were calculated by linear regression analysis. The selective ACHE inhibitor BW284C51 and the CHE inhibitor iso-OMPA were both used in final concentration of $10^{-5}$M to distinguish between ACHE and CHE activities, as detailed previously 161,70,77).

c. The approximate extent of ACHE and CHE gene amplification, as well as the amplification of C-RAFI, C-FES, V-SIS and C-MYC oncogenes was determined by dot-blot DNA hybridization followed by optical densitometry. Quantities of the labeled ACHEcDNA and ChEcDNA or oncogene DNA probes that hybridized with genomic corresponding DNA sequences in each tissue sample are presented in value equivalent to pg of the relevant cDNA per µg of genomic DNA. Measurements of ACHE and CHE gene quantification in peripheral blood DNA samples were performed as described (72) and compared to parallel levels determined in a healthy control (Sample No. 20). Both the level and the DNA blot hybridization patterns of the ACHE and the CHE genes were similar in control blood DNA to those observed for DNA from normal ovary (sample 17 and Ref. (71)).

N.A.—not applicable, N.D.—not determined.

TABLE III

| Quantitation of CHE gene amplification and enzyme activities in ovarian tissue homogenates | | | | | | | | | | | |
|---|---|---|---|---|---|---|---|---|---|---|---|
| | | Enzyme activities[b] nmol/min/gr | | | | | | | | | |
| | | ACHE | | CHE | | | | | | | |
| Tumor classification | | | Membrane | | Membrane | Amplified Genes, pg/µg DNA[c] | | | | | |
| No and age | | Soluble | associated | Soluble | associated | CHE | ACHE | RAF1 | SIS | FES | MYC |
| A. Malignant ovarian tumors[a] | | | | | | | | | | | |
| 1 Serous Papillary ad.ca | (57) | 657 | 251 | 381 | 28 | 32–38 | 4–6 | 40–50 | 20–30 | 10–12 | 1–2 |
| 2 Serous Papillary ad.ca | (54) | 105 | 27 | 119 | 17 | 21–26 | 10–13 | 2–3 | 1–2 | 1–2 | 1–2 |
| 3 Serous Papillary ad.ca | (22) | 980 | 183 | 412 | 33 | 20–24 | 8–12 | 2–3 | 1–2 | 1–2 | 1–2 |
| 4 Serous Papillary ad.ca | (55) | 607 | 218 | 397 | 31 | 7–11 | N.D | N.D | N.D | N.D | N.D |
| 5 Non-differentiated ad.ca | (44) | 1005 | 124 | 192 | 14 | 50–60 | 7–11 | 60–80 | 40–50 | 40–60 | 2–3 |
| 6 Non-differentiated ad.ca | (49) | 283 | 85 | 203 | 13 | 6–8 | 4–6 | 3–4 | 1–2 | 1–2 | 1–2 |
| 7 Non-differentiated ad.ca | (67) | 207 | 58 | 183 | 11 | 4–6 | 6–8 | 5–8 | 20–30 | 1–2 | 1–2 |
| 8 Endometrioid ad.ca | (43) | 451 | 18 | 219 | 10 | 30–40 | 9–12 | 60–80 | 40–50 | 10–12 | 2–3 |
| 9 Endometrioid ad.ca | (52) | 311 | 85 | 197 | 11 | 6–9 | N.D | N.D | N.D | N.D | N.D |
| 10 Moucinous ad.ca | (87) | 193 | 81 | 128 | 7 | 5–10 | N.D | N.D | N.D | N.D | N.D |
| 11 Granulosa cell tumor | (42) | 428 | 203 | 212 | 5 | 40 . 50 | 18–23 | 5–8 | 1–3 | 1–2 | 1–2 |

TABLE III-continued

Quantitation of CHE gene amplification and enzyme activities in ovarian tissue homogenates

| Tumor classification No and age | | Enzyme activities[b] nmol/min/gr | | | | Amplified Genes, pg/μg DNA[c] | | | | | |
|---|---|---|---|---|---|---|---|---|---|---|---|
| | | ACHE | | CHE | | | | | | | |
| | | Soluble | Membrane associated | Soluble | Membrane associated | CHE | ACHE | RAF1 | SIS | FES | MYC |
| B. Benign ovarian tumors | | | | | | | | | | | |
| 12 Follicular cyst | (47) | 208 | 53 | 211 | 6 | 5–7 | N.D | N.D | N.D | N.D | N.D |
| 13 Follicular cyst | (48) | 412 | 183 | 222 | 5 | N.D | N.D | N.D | N.D | N.D | N.D |
| 14 Follicular cyst | (46) | 298 | 89 | 232 | 4 | 5–7 | N.D | N.D | N.D | N.D | N.D |
| 15 Follicular cyst | (36) | 753 | 412 | 361 | 6 | 5–7 | N.D | N.D | N.D | N.D | N.D |
| 16 Dermoid cyst | (35) | 818 | 453 | 377 | 37 | 5–7 | N.D | N.D | N.D | N.D | N.D |
| C. Others | | | | | | | | | | | |
| 17 Normal ovary (Uterine myoma) | (48) | 213 | 89 | 106 | 4 | 2–5 | N.D | N.D | N.D | N.D | N.D |
| 18 Normal ovary (Uterine myoma) | (47) | 187 | 45 | 123 | 4 | 1–3 | N.D | N.D | N.D | N.D | N.D |
| 19 Benign ovary of No. 6 | (49) | 192 | 35 | 138 | 5 | 3–7 | 4–6 | 5–8 | 5–10 | 3–4 | 1–2 |
| 20 Peripheral Blood, (no pathologies) | (37) | N.A. | N.A. | N.A. | N.A | 1–3 | 1–3 | N.D | N.D | N.D | N.A |

LIST OF REFERENCES

1. Silver, A., The Biology of Cholinesterases. North-Holland Pub. Co., Amsterdam (1974).
2. Heymann, E., Carboxylesterases and Amidases. In: W. Jackoby, Ed., Enzymatic Basis of Detoxification, Vol. 2, Acad. Press, N.Y. pp. 291–323 (1980).
3. Massoulie, J. and Bon, S., Ann. Rev. Neurosci. 5: 57–106 (1982).
4. Silman, I. and Futerman, T. H., Eur. J. Biochem. 170: 11–22 (1987).
5. Soreq, H. and Gnatt, A., Molecular Neurobiol. 1: 47–80 (1987).
6. Koelle, G. B., Anticholinesterases Agents, In: Goodman, L. S. and Gilman, A., Eds. Fifth Ed.,McMillan, N.Y., pp. 445–466 (1972).
7. Aidridge, W. N. and Reiner, E., Enzyme Inhibitors as Substrates, North Holland, Amsterdam (1972).
8. Dayhoff, M. O. et al., Methods Enzymol. 91: 524–545 (1983).
9. Lockridge, O. and LaDu, B. N., Biochem. Genet. 24: 485–498 (1986).
10. Austin, L. and Berry, W. K., Biochem. J. 54: 694–700 (1953).
11. Toutant, J. P. and Massoulie, J. (1988), Acetylcholinesterase, In: Kenny, Turner (Eds.): Mammalian Ectoenzymes, Hooland, Elsevier Science Publishers, BW 1985, 289–328.
12. Silman, I., et al., Nature 28: 160–161 (1979).
13. Whittaker, M., Cholinesterase. Monographs in Human Genetics, Vol. 11, Karger (Basel) Pub.(1986).
14. Zakut, H., et al., J. Neurochem. 45: 382–389 (1985).
15. Coyle, J. T. et al., Science 219: 1184–1190 (1983).
16. Sikorav, J. L., et al., EMBO J. 6: 1865–1873 (1987).
17. Schumacher M. et al., Nature 319: 407–409 (1986).
18. Hall, L. M. and Spierer, P., EMBO J. 5: 2949–2954 (1987).
19. Oakeshott, J. G., et al., Proc. Natl. Acad. Sci. U.S.A. 84: 3359–3363 (1987).
20. Prody, C. et al., Proc. Natl. Acad. Sci. U.S.A. 84: 3555–3559 (1987).
21. McTiernan, C. et al., Proc. Natl. Acad. Sci. U.S.A. 84: 6682–6686 (1987).
22. UN Security Council, Report of Specialists Appointed by the Secretary General, Paper No. S/16433 (1984).
23. Bidstrup, P. L., British Med. J. Sept. 2, 548–551 (1950).
24. Namba, T. et al., The Am. J. Med. 50: 475–492 (1971).
25. Bull, D., The Growing Problem: Pesticides and the Third World Poor, Oxford, U.K.: OXFAM, 38–45 (1982).
26. Tanimura, T. et al., Arch. Environ. Health 15: 609–613 (1967).
27. Ogi, D. and Hamada, A., J. Jpn. Obstet. Gynecol. Soc. 17: 569 (1965).
28. Hall, J. G. et al., Am. J. Med. Genet. 7: 47–74 (1980).
29. Loomis, T. A., Toxicol. Appl. Pharmacol. 5: 489–499 (1963).
30. Doctor, B. P., et al., PNAS 80: 5767–5771 (1983).
31. Klose, R. and Gustensohn, G., Prakl. Anasthe. II, 1–7 (1976).
32. Thompson, J. C. and Whittaker M., Acta Genet. 16: 206–215 (1966).
33. Kalow, W. and Gunn, D. R., Ann. Hum. Genet. (Lond.) 23: 239–248 (1959).
34. Whittaker, M., Anaesthesia 35: 174–197 (1980).
35. Hodgkin, W. E., et al., J. Clin. Invest. 44: 486–497 (1965).
36. Szeinberg, A., et al., Clin. Genet. 3: 123–127 (1965).
37. Soreq, H. and Zakut, H., Monographs in Human Genetics, Vol. 13, Karger, Basel, (1990, in press).
38. Soreq, H. and Zakut, H., Pharm. Res. 7: 1–7 (1990).
39. Spokes, E. G. S., Brain 103: 179–183 (1980).
40. Atack, J. R., et al., Neurosci. Lett. 40: 199–204 (1983).
41. Rakonczay, Z. et al., Subcellular Biochemistry 12: 335–378, Harris, J. R., Ed. Plenum Press, N.Y. (1988).
42. Layer, P. G. et al., J. Neurochem. 49: 175–182 (1987).
43. Paulus, J. P. et al., Blood 58: 1100–1106 (1981).
44. Burstein, S. A., et al., J. Cell Physiol. 103: 201–208 (1980).
45. Burstein, S. A., et al., J. Cell Physiol. 122: 159–165 (1985).
46. Burstein, S. A., et al., Clin. Haematol. 12: 3–27 (1983).
47. Soreq, H., et al., Hum. Genet. 77: 325–328 (1987).
48. Bernstein, R., et al., Blood 60: 613–617 (1982).
49. Turchini, M. F., et al., Cancer Genet. Cytogenet. 20: 1–4 (1986).

50. Pintado, T., et al., Cancer 55: 535–541 (1985).
51. Bishop, J. M., Science 235: 305–311 (1987).
52. Corner et al., Proc. Natl. Acad. Sci. U.S.A. 80: 278–282 (1983).
53. Prody, C., et al., J. Neurosci. Res. 16: 25–35 (1986).
54. Lockridge, O., et al., J. Biol. Chem. 262: 549–557 (1987).
55. Merken, L., et al., Nature 316: 647–651 (1985).
56. Hass and Rosenberrry, T. L., Anal. Bio. Chem. 148: 74–77 (1985).
57. Maizel, J. V., et al., Proc. Natl. Acad. Sci. U.S.A. 78: 7665–7669 (1981).
58. Hopp, T. P. and Woods, K. R., Proc. Natl. Acad. Sci. U.S.A. 78: 3824–3828 (1981).
59. McPhee-Quigley, K. et al., J. Biol. Chem. 260: 12185–12189 (1986).
60. Lockridge, O. et al.,. J. Biol. Chem. 262: 549–557 (1987).
61. Soreq, H., et al., EMBO J. 3: 1371–1375 (1984).
62. Kostovic, I. and Rakic, P., J. Neurosci. 4: 25–42 (1984).
63. Zakut, H., et al., Hum. Rep. (1990), in press.
64. Soreq, H. and Prody, C. A., In: Computer-Assisted Modeling of Receptor-Ligand Interactions, Theoretic Aspects and Application to Drug Design, Golombek A. and Rein, R., Eds., Alan & Liss, N.Y. (1989), 347–359.
65. Soreq, H. and Zakut, H. (1989), Expression and in vivo amplification of the human cholinesterase genes, Progress in Brain Research, (in press).
66. Drews, E., Prog. Histochem. 7: 1–52 (1975).
67. Razon, N., et al., Exp. Neurol. 84: 681–695 (1984).
68. Slotman, B. J. and Ramanath, R. B. Anticancer Res. 8: 417–434 (1988).
69. Prody, C. A., et al., Proc. Natl. Acad. Sci. U.S.A., 86: 690–694 (1989).
70. Dreyfus, P., et al., J. Neurochem. 51: 1858–1867 (1988).
71. Malinger, G., et al., J. Molec. Neurosci. 1: 77–84 (1989).
72. Lapidot-Lifson, Y., et al., Proc. Natl. Acad. Sci. U.S.A. 86: 4715–4719 (1989).
73. Gnatt, A. and Soreq, H. (1987) Molecular Cloning of Human Cholinesterase Genes: Potential Applications in Neurotoxicology. In: Model Systems in Neurotoxicology: Alternative Approaches to Animal Testing. Eds. A. Shaher and A. M. Goldberg, Alan R. Liss, Inc., New York, 111–119.
74. McGuire, M. C., et al., Proc. Natl. Acad. Sci. U.S.A. 86: 953–957 (1989).
75. Chatonnet, A. and Lockridge, O., Biochem. J. 260: 625–634 (1989).
76. Zakut, H., et al., Cancer 61: 727–739 (1988).
77. Soreq, H., et al., J. Biol. Chem. 264: 10608–10613 (1989).
78. Mollgard, K., et al., Dev. Biol. 128: 207–221 (1988).
79. Soreq, H., et al., Human Reprod. 2: 689–693 (1987).
80. Gnatt, A. et al., Human Acetylcholinesterase and Butyrylcholinesterase are Encoded by Two Distinct Enzymes, Cell. Molec. Neurobiol. (1990, in press).

What is claimed is:

1. A substantially pure polynucleotide having a sequence encoding human acetylcholinesterase.

2. An expression vector comprising the nucleotide sequence of claim 1.

3. A host cell transformed with the expression vector of claim 2.

4. The host cell of claim 3 being a eukaryotic cell.

5. The host cell of claim 4 selected from the group consisting of embryonic or nervous system cells.

6. The host cell of claim 4 being a non-mammalian cell.

7. A host cell containing a non-naturally occurring recombinant nucleotide construct, wherein said construct comprises a sequence (A) encoding human acetylcholinesterase operably linked to a control sequence (B) such that (B) regulates (A) expression to cause the host cell to produce active human acetylcholinesterase.

8. The host cell according to claim 7 in which the nucleotide sequence (A) encoding the human acetylcholinesterase comprises the nucleotide sequence as depicted in FIG. 1f, FIG. 1g.

9. A substantially pure nucleotide sequence encoding an acetylcholinesterase, whose polypeptide sequence comprises the polypeptide sequence depicted in FIG. 1k, FIG. 1l from amino acid residue number 1 to amino acid residue number 613.

10. A substantially pure nucleotide sequence encoding an acetylcholinesterase, wherein said sequence comprises the nucleotide sequence depicted in FIG. 1f, FIG. 1g from nucleotide residue 169 to nucleotide residue 1998.

11. A substantially pure nucleotide sequence encoding a human acetylcholinesterase, wherein said sequence selectively hybridizes to the nucleotide sequence depicted in FIG. 1f, FIG. 1g from nucleotide residue 169 to nucleotide residue 1998.

12. The nucleotide sequence according to claim 1, 9, 10 or 11 wherein said sequence comprises genomic DNA.

13. The nucleotide sequence according to claim 1, 9, 10 or 11 wherein said sequence comprises cDNA.

14. The nucleotide sequence according to claim 1, 9, 10 or 11 wherein said sequence comprises mRNA.

15. An expression vector comprising the nucleotide sequence of claim 1, 9, 10 or 11.

16. A host cell transformed with the expression vector of claim 15.

17. The host cell of claim 16 being a eukaryotic cell.

18. The host cell of claim 17 selected from the group consisting of embryonic or nervous system cells.

19. The host cell of claim 17 being a non-mammalian cell.

* * * * *